US012075780B2

(12) United States Patent
Nesvadba et al.

(10) Patent No.: US 12,075,780 B2
(45) Date of Patent: *Sep. 3, 2024

(54) USE OF ALKOXYPYRAZOLES AS NITRIFICATION INHIBITORS

(71) Applicant: BASF SE, Ludwigshafen (DE)

(72) Inventors: Peter Nesvadba, Basel (CH); Allan F. Cunningham, Basel (CH); Barbara Nave, Limburgerhoff (DE); Olof Wallquist, Basel (CH); Alexander Wissemeier, Limburgerhoff (DE); Shrirang Hindalekar, Mumbai (IN); Tejas Pothi, Mumbai (IN)

(73) Assignee: BASF SE, Ludwigshafen (DE)

( * ) Notice: Subject to any disclaimer, the term of this patent is extended or adjusted under 35 U.S.C. 154(b) by 723 days.

This patent is subject to a terminal disclaimer.

(21) Appl. No.: 16/969,705

(22) PCT Filed: Feb. 28, 2019

(86) PCT No.: PCT/EP2019/055007
§ 371 (c)(1),
(2) Date: Aug. 13, 2020

(87) PCT Pub. No.: WO2019/166561
PCT Pub. Date: Sep. 6, 2019

(65) Prior Publication Data
US 2021/0000115 A1   Jan. 7, 2021

(30) Foreign Application Priority Data

Feb. 28, 2018   (EP) .................................... 18159322

(51) Int. Cl.
*A01N 43/58* (2006.01)
*C05C 9/00* (2006.01)
*C07D 231/20* (2006.01)

(52) U.S. Cl.
CPC ............... *A01N 43/58* (2013.01); *C05C 9/00* (2013.01); *C07D 231/20* (2013.01)

(58) Field of Classification Search
None
See application file for complete search history.

(56) References Cited

U.S. PATENT DOCUMENTS

| 3,635,690 | A | * | 1/1972 | Griffith | .................... C05G 3/90 |
| | | | | | 71/902 |
| 4,000,301 | A | * | 12/1976 | Walworth | ............ C07D 231/18 |
| | | | | | 548/370.7 |
| 6,139,596 | A | | 10/2000 | Barth et al. | |
| 10,676,408 | B2 | | 6/2020 | Nave et al. | |
| 11,498,885 | B2 | * | 11/2022 | Nesvadba | ................. C05C 9/00 |
| 2012/0202834 | A1 | | 8/2012 | Aspnes et al. | |
| 2018/0208520 | A1 | * | 7/2018 | Barr | ........................ C05G 3/90 |

FOREIGN PATENT DOCUMENTS

| AU | 2015227487 B1 | 12/2015 |
| CN | 103370306 A | 10/2013 |
| DE | 222471 | 5/1985 |
| JP | S47-047183 | 11/1972 |
| JP | 2000-515479 A | 11/2000 |
| JP | 2018504350 A | 2/2018 |
| RU | 2618116 C1 | 5/2017 |
| SU | 1198049 A1 | 12/1985 |
| SU | 1470737 A1 | 4/1989 |

OTHER PUBLICATIONS

B. Madhavilatha, "Synthesis of 1,2,3-triazole and isoxazole-linked pyrazole hybrids and their cytotoxic activity", Med Chem Res (2017) 26:1753-1763.*
Parkhomenko et al., Kinetics of the thermolysis of nitrification inhibitors based on 3(5)-methylpyrazole derivatives, Zhurnal Prikladnoi Khimii, 65(6):1362-7 (1992).
Sharma et al., Synthesis and evaluation of some pyrazoles for N-regulation of soil-applied urea in rice-wheat culture, Pesticide Research Journal, 18(1):7-11 (Jan. 2006).
International Application No. PCT/EP2019/055007, International Search Report and Written Opinion, mailed Apr. 29, 2019.
Parchment et al., The prediction of tautomer equilibira in hydrated 3-hydroxypyrazole: A challenge to theory, J. Am. Chem. Soc., 115:2351-6 (1993).
Guillou et al., An improved preparation of 3-alkoxypyrazoles, Synthesis, No. 21, pp. 3504-8 (2008).

* cited by examiner

*Primary Examiner* — Wayne A Langel
(74) *Attorney, Agent, or Firm* — MARSHALL, GERSTEIN & BORUN LLP

(57) ABSTRACT

The present invention relates to nitrification inhibitors of formula (I), which are alkoxypyrazole compounds. Moreover, the invention relates to the use of compounds of formula (I) as nitrification inhibitors, i.e. for reducing nitrification, as well as agro-chemical mixtures and compositions comprising the nitrification inhibitors of formula (I).

12 Claims, No Drawings

USE OF ALKOXYPYRAZOLES AS NITRIFICATION INHIBITORS

CROSS-REFERENCE TO RELATED APPLICATIONS

This is U.S. national phase of International Application No. PCT/EP2019/055007, filed Feb. 28, 2019, which claims the benefit of European Patent Application No. 18159322.9, filed Feb. 28, 2018.

The present invention relates to novel nitrification inhibitors of formula I, which are alkoxypyrazole compounds. Moreover, the invention relates to the use of compounds of formula I as nitrification inhibitors, i.e. for reducing nitrification, as well as agrochemical mixtures and compositions comprising the nitrification inhibitors of formula I. Further encompassed by the present invention are methods for reducing nitrification, said methods comprising the treatment of plants, soil and/or loci where the plant is growing or is intended to grow with said nitrification inhibitor and methods for treating a fertilizer or a composition by applying said nitrification inhibitor.

Nitrogen is an essential element for plant growth and reproduction. About 25% of the plant available nitrogen in soils (ammonium and nitrate) originate from decomposition processes (mineralization) of organic nitrogen compounds such as humus, plant and animal residues and organic fertilizers. Approximately 5% derive from rainfall. On a global basis, the biggest part (70%), however, is supplied to the plant by inorganic nitrogen fertilizers. The mainly used nitrogen fertilizers comprise ammonium compounds or derivatives thereof, i.e. nearly 90% of the nitrogen fertilizers applied worldwide is in the $NH_4^+$ form (Subbarao et al., 2012, Advances in Agronomy, 114, 249-302). This is, inter alia, due to the fact that $NH_4^+$ assimilation is energetically more efficient than assimilation of other nitrogen sources such as $NO_3^-$. Moreover, being a cation, $NH_4^+$ is held electrostatically by the negatively charged clay surfaces and functional groups of soil organic matter. This binding is strong enough to limit $NH_4^+$-loss by leaching to groundwater. By contrast, $NO_3^-$, being negatively charged, does not bind to the soil and is liable to be leached out of the plants' root zone. In addition, nitrate may be lost by denitrification which is the microbiological conversion of nitrate and nitrite ($NO_2^-$) to gaseous forms of nitrogen such as nitrous oxide ($N_2O$) and molecular nitrogen ($N_2$). However, ammonium ($NH_4^+$) compounds are converted by soil microorganisms to nitrates ($NO_3^-$) in a relatively short time in a process known as nitrification. The nitrification is carried out primarily by two groups of chemolithotrophic bacteria, ammonia-oxidizing bacteria (AOB) of the genus *Nitrosomonas* and *Nitrobacter*, which are ubiquitous component of soil bacteria populations. The enzyme, which is essentially responsible for nitrification is ammonia monooxygenase (AMO), which was also found in ammonia-oxidizing archaea (Subbarao et al., 2012, Advances in Agronomy, 114, 249-302).

The nitrification process typically leads to nitrogen leakage and environmental pollution. As a result of the various losses, approximately 50% of the applied nitrogen fertilizers are lost during the year following fertilizer addition (see Nelson and Huber; Nitrification inhibitors for corn production (2001), National Corn Handbook, Iowa State University).

As countermeasure, the use of nitrification inhibitors, mostly together with fertilizers, was suggested. Suitable nitrification inhibitors include biological nitrification inhibitors (BNIs) such as linoleic acid, alpha-linolenic acid, methyl p-coumarate, methyl ferulate, MHPP, Karanjin, brachialacton or the p-benzoquinone sorgoleone (Subbarao et al., 2012, Advances in Agronomy, 114, 249-302). Further suitable nitrification inhibitors are synthetic chemical inhibitors such as nitrapyrin, dicyandiamide (DCD), 3,4-dimethyl pyrazole phosphate (DMPP), 4-amino-1,2,4-triazole hydrochloride (ATC), 1-amido-2-thiourea (ASU), 2-amino-4-chloro-6-methylpyrimidine (AM), 5-ethoxy-3-trichloromethyl-1,2,4-thiodiazole (terrazole), or 2-sulfanilamidothiazole (ST) (Slangen and Kerkhoff, 1984, Fertilizer research, 5(1), 1-76).

However, many of these inhibitors only work sub-optimal. In addition, the world population is expected to grow significantly in the next 20-30 years, and, therefore, food production in sufficient quantities and quality is necessary. In order to achieve this, the use of nitrogen fertilizers would have to double by 2050. For environmental reasons, this is not possible, since nitrate levels in drinking water, eutrophication of surface water and gas emissions into the air have already reached critical levels in many places, causing water contamination and air pollution. However, fertilizer efficiency increases significantly and less fertilizer may therefore be applied, if nitrification inhibitors are used. Therefore, there is a clear need for novel nitrification inhibitors, as well as for methods using them.

Sharma et al. (JP Sharma, HK Taneja, SS Tomar Pesticide Research Journal, 2006, 18(1), 7-11) inter alia discloses 3-ethoxy-5-methylpyrazole as nitrification inhibitor. However, it has been found that this compound has a high volatility and is therefore disadvantageous for long-term applications.

It was an object of the present invention to provide improved nitrification inhibitors.

In particular, it was an object of the present invention to provide nitrification inhibitors, which have a high activity as nitrification inhibitors in comparison to the nitrification inhibitors described in the prior art.

Furthermore, it was an object of the present invention to provide nitrification inhibitors, which have a reduced volatility.

Furthermore, it was an object of the present invention to provide nitrification inhibitors, which may cost-effectively be prepared, and which are environmentally safe.

It has surprisingly been found that at least one of these objects can be achieved by using the nitrification inhibitors according to the present invention, which are alkoxypyrazole compounds of formula I

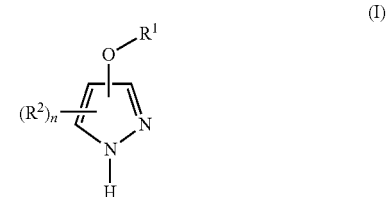

(I)

or the salts, stereoisomers, tautomers, or N-oxides thereof, wherein $R^1$ is $C_1$-$C_6$-alkyl, $C_3$-$C_6$-cycloalkyl, benzyl, allyl, propargyl, $CHR^aC(=O)OR^b$, $CHR^aC(=O)NR^bR^c$, or phenyl, wherein said phenyl group is unsubstituted or substituted by one or more, same or different substituents $R^x$;

$R^2$ is halogen, $C_1$-$C_6$-alkyl, $C_1$-$C_3$-alkoxy, $C_3$-$C_6$-cycloalkyl, allyl, propargyl, benzyl, or phenyl, wherein said phenyl group is unsubstituted or substituted by one or more, same or different substituents $R^x$;
and wherein
$R^a$ is H, $C_1$-$C_4$-alkyl, $C_1$-$C_4$-haloalkyl, $C_3$-$C_8$-cycloalkyl, phenyl, or phenyl-$C_1$-$C_2$-alkyl;
$R^b$ is H, $C_1$-$C_4$-alkyl, $C_1$-$C_4$-haloalkyl, $C_3$-$C_8$-cycloalkyl, phenyl, or phenyl-$C_1$-$C_2$-alkyl;
$R^c$ is H, $C_1$-$C_4$-alkyl, $C_1$-$C_4$-haloalkyl, or phenyl;
$R^x$ is halogen, $C_1$-$C_4$-alkyl, $C_1$-$C_4$-haloalkyl, $C_1$-$C_4$-alkoxy, or $C_1$-$C_4$-haloalkoxy;
n is 0, 1, or 2.

The inventors surprisingly found that by applying the compounds of formula I as defined above and hereinafter the nitrification of ammonium to nitrate can significantly be reduced.

Thus, according to one embodiment, the present invention relates to the use of an alkoxypyrazole compound of formula I

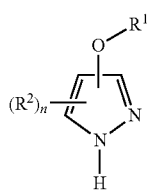

(I)

or a salt, stereoisomer, tautomer, or N-oxide thereof as a nitrification inhibitor,
wherein
$R^1$ is $C_1$-$C_6$-alkyl, $C_3$-$C_6$-cycloalkyl, benzyl, allyl, propargyl, $CHR^aC(=O)OR^b$, $CHR^aC(=O)NR^bR^c$, or phenyl, wherein said phenyl group is unsubstituted or substituted by one or more, same or different substituents $R^x$;
$R^2$ is halogen, $C_1$-$C_6$-alkyl, $C_1$-$C_3$-alkoxy, $C_3$-$C_6$-cycloalkyl, allyl, propargyl, benzyl, or phenyl, wherein said phenyl group is unsubstituted or substituted by one or more, same or different substituents $R^x$;
and wherein
$R^a$ is H, $C_1$-$C_4$-alkyl, $C_1$-$C_4$-haloalkyl, $C_3$-$C_8$-cycloalkyl, phenyl, or phenyl-$C_1$-$C_2$-alkyl;
$R^b$ is H, $C_1$-$C_4$-alkyl, $C_1$-$C_4$-haloalkyl, $C_3$-$C_8$-cycloalkyl, phenyl, or phenyl-$C_1$-$C_2$-alkyl;
$R^c$ is H, $C_1$-$C_4$-alkyl, $C_1$-$C_4$-haloalkyl, or phenyl;
$R^x$ is halogen, $C_1$-$C_4$-alkyl, $C_1$-$C_4$-haloalkyl, $C_1$-$C_4$-alkoxy, or $C_1$-$C_4$-haloalkoxy;
n is 0, 1, or 2.

In one preferred embodiment of said use, in said compound of formula I, the alkoxypyrazole compound of formula I is present in the form of a pyrazolium salt, preferably in the form of a pyrazolium phosphate salt.

In another preferred embodiment of said use, in said compound of formula I $R^1$ is allyl, $C_1$-$C_3$-alkyl, preferably $C_1$-$C_2$-alkyl.

In another preferred embodiment of said use, in said compound of formula I $OR^1$ is present in the 3- or 5-position of the pyrazole ring.

In another preferred embodiment of said use, in said compound of formula I n is 1, and $R^2$ is present in the 4-position of the pyrazole ring; or
n is 1, and $R^2$ is present in the 5- or 3-position of the pyrazole ring; or
n is 0, i.e. $R^2$ is absent.

In a further aspect, the present invention relates to a composition for use in reducing nitrification comprising at least one compound of formula I as defined above and at least one carrier.

In a further aspect, the present invention relates to an agrochemical mixture comprising at least one fertilizer and at least one compound of formula I as defined above; or at least one fertilizer and a composition as mentioned above for use in reducing nitrification.

In a preferred embodiment, said compound of formula I as defined above is used in combination with a fertilizer for reducing nitrification. In a further specific embodiment, said compound of formula I as defined above is used for reducing nitrification in combination with a fertilizer in the form of an agrochemical mixture as mentioned above. In a further preferred embodiment, said reduction of nitrification as mentioned above occurs in or on a plant, in the root zone of a plant, in or on soil or soil substituents and/or at the locus where a plant is growing or is intended to grow.

In another aspect, the present invention relates to a method for reducing nitrification, comprising treating a plant growing on soil or soil substituents and/or the locus or soil or soil substituents where the plant is growing or is intended to grow with at least one compound of formula I as defined above, or with an agrochemical composition as defined above. In a preferred embodiment of the method, the plant and/or the locus or soil or soil substituents where the plant is growing or is intended to grow is additionally provided with a fertilizer. In a further preferred embodiment of the method, the application of the nitrification inhibitor, i.e. the compound of formula I, and of said fertilizer is carried out simultaneously or with a time lag. In a particularly preferred embodiment, said time lag is an interval of 1 day, 2 days, 3 days, 1 week, 2 weeks or 3 weeks. In case of application with a time lag, the nitrification inhibitor may be applied first and then the fertilizer. In a further preferred embodiment of the method, in a first step the nitrification inhibitor as defined above is applied to seeds, to a plant and/or to the locus where the plant is growing or is intended to grow and in a second step the fertilizer is applied to a plant and/or to the locus where the plant is growing or is intended to grow, wherein the application of a said nitrification inhibitor in the first step and the fertilizer in the second step is carried out with a time lag of at least 1 day, 2 days, 3 days, 4 days, 5 days, 6 days, 1 week, 2 weeks or 3 weeks. In other embodiments of application with a time lag, a fertilizer may be applied first and then the nitrification inhibitor as defined above may be applied. In a further preferred embodiment of the method, in a first step a fertilizer is applied to a plant and/or to the locus where the plant is growing or is intended to grow and in a second step the nitrification inhibitor as defined above is applied to seeds, to a plant and/or to the locus where the plant is growing or is intended to grow, wherein the application of a said fertilizer in the first step and said nitrification inhibitor in the second step is carried out with a time lag of at least 1 day, 2 days, 3 days, 4 days, 5 days, 6 days, 1 week, 2 weeks or 3 weeks.

In another aspect, the present invention relates to a method for treating a fertilizer, comprising the application of a nitrification inhibitor as defined above; or to a method for treating a composition as defined above, comprising the application of a nitrification inhibitor as defined above.

In a preferred embodiment of the use, the agrochemical mixture or method of the invention, said fertilizer is a solid or liquid ammonium-containing inorganic fertilizer such as NPK fertilizer, ammonium nitrate, calcium ammonium nitrate, ammonium sulfate nitrate, ammonium sulfate or ammonium phosphate; a solid or liquid organic fertilizer such as liquid manure, semi-liquid manure, biogas manure, stable manure and straw manure, worm castings, compost, seaweed or guano, or an urea-containing fertilizer such as urea, formaldehyde urea, anhydrous ammonium, urea ammonium nitrate (UAN) solution, urea sulphur, urea based NPK-fertilizers, or urea ammonium sulfate.

In a further preferred embodiment of the use or method of the invention, said plant is an agricultural plant such as wheat, barley, oat, rye, soybean, corn, potatoes, oilseed, rape, canola, sunflower, cotton, sugar cane, sugar beet, rice, or a vegetable such as spinach, lettuce, asparagus, or cabbages; or sorghum; a silvicultural plant; an ornamental plant; or a horticultural plant, each in its natural or in a genetically modified form.

The compounds of formula I can be prepared by standard processes of organic chemistry. Suitable methods for preparing pyrazole compounds in general are described in "Progress in Heterocyclic Chemistry", Vol. 27, G. W. Gribble, J. A. Joule, Elsevier, 2015, Chapter 5.4.2.

The $OR^1$ group may be introduced by selecting suitable starting materials for the pyrazole ring formation.

A general method for the synthesis of 3-alkoxy-pyrazoles comprises the reaction between hydrazine hydrochloride and various β-ketoesters as described by, for example: a) Sadrine Guillou, Frédéric J. Bonhomme, Yves L. Janin, Synthesis 2008, 3504-3508; or b) in WO 2010/015657 A2, and as shown below:

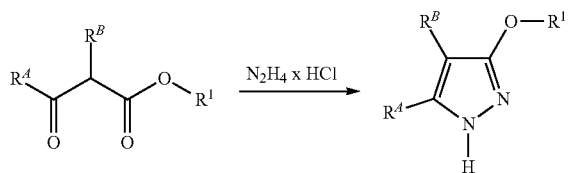

$R^A$ and $R^B$ may be hydrogen or may have any of the meaning provided above for $R^2$.

Further, the 3-alkoxy group can be introduced by alkylating a suitable hydroxypyrazole derivative as described e.g. by a) D. Piomelli and coworkers, Synthesis 2016, 2739-2756, or b) Sandrine Guillou, Yves L. Janin, Chem. Eur. J. 2010, 16, 4669-4677.

Diverse methods to synthesize pyrazoles bearing the alkoxy group in the position 4 were described by William F. Vernier, Laurent Gomez, Tetrahedron Letters 2017, 4587-4590.

The substituent $R^2$ may be introduced by standard reactions including aromatic substitution reactions, or by selecting suitable starting materials for the pyrazole ring formation.

It is to be understood that 1H-pyrazoles, especially those with different substituents in 3- and 5-position, may be present in the form of different annular tautomers, i.e. prototrophic tautomers, as described by a) Schaumann, Ernst, Methoden der Organischen Chemie, 1994, Houben-Weyl, E8b: Hetarene III and b) A. Güven, N. Kaniskan, Journal of Molecular Structure (Theochem), 1999, 488, 125-134.

It is to be understood that these annular tautomers of the compounds of formula I may be formed, as the hydrogen atom may migrate to the other nitrogen atom and vice versa.

Furthermore, it is to be understood that the compounds of formula I may be present in the form of the different annular tautomers, or as a mixture thereof. Further, it is to be understood that the equilibrium between those tautomeric forms depends on the steric and electronic properties of the substituents present on the pyrazole ring of the compounds of formula I. Therefore, if pyrazolium ions of the compounds of formula I are formed, the different tautomers will typically result in two different isomers of the pyrazolium ion. In certain preferred embodiments of the invention, such isomer mixtures of pyrazolium ions of the compounds of formula I may be used as nitrification inhibitors.

Before describing in detail exemplary embodiments of the present invention, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

The term "nitrification inhibitor" is to be understood in this context as a chemical substance which slows down or stops the nitrification process. Nitrification inhibitors accordingly retard the natural transformation of ammonium into nitrate, by inhibiting the activity of bacteria such as Nitrosomonas spp. The term "nitrification" as used herein is to be understood as the biological oxidation of ammonia ($NH_3$) or ammonium ($NH_4^+$) with oxygen into nitrite ($NO_2^-$) followed by the oxidation of these nitrites into nitrates ($NO_3^-$) by microorganisms. Besides nitrate ($NO_3^-$) nitrous oxide is also produced through nitrification. Nitrification is an important step in the nitrogen cycle in soil. The inhibition of nitrification may thus also reduce N$_2$O losses. The term nitrification inhibitor is considered equivalent to the use of such a compound for inhibiting nitrification. The term "compound(s) according to the invention", or "compounds of formula I" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

Depending on the substitution pattern, the compounds according to the invention may have one or more centers of chirality, in which case they are present as mixtures of enantiomers or diastereomers. The invention provides both the single pure enantiomers or pure diastereomers of the compounds according to the invention, and their mixtures and the use according to the invention of the pure enantiomers or pure diastereomers of the compounds according to the invention or their mixtures. Suitable compounds according to the invention also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula I, i.e. to single enantiomers or diastereomers, as well as to mixtures thereof.

The compounds of formula I may be amorphous or may exist in one or more different crystalline states (polymorphs) which may have different macroscopic properties such as stability or show different biological properties such as activities. The present invention relates to amorphous and crystalline compounds of formula I, mixtures of different crystalline states of the respective compound I, as well as amorphous or crystalline salts thereof.

Salts of the compounds of the formula I are preferably agriculturally acceptable salts. They can be formed in a customary manner, e.g. by reacting the compound with an acid of the anion in question if the compound of formula I has a basic functionality. Agriculturally useful salts of the compounds of formula I encompass especially the acid addition salts of those acids whose cations and anions, respectively, have no adverse effect on the mode of action of the compounds of formula I. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of C$_1$-C$_4$-alkanoic acids, preferably formate, acetate, propionate and butyrate. They can preferably be formed by reacting compounds of formula I with an acid of the corresponding anion, preferably of hydrochloric acid, hydrobromic acid, sulfuric acid, phosphoric acid or nitric acid. Preferred salts of the compounds of formula I are phosphate salts.

The term "N-oxide" includes any compound of formula I, wherein a tertiary nitrogen atom, e.g. the pyridine nitrogen atom, is oxidized to an N-oxide moiety.

Tautomers of the compounds of formula I may be present, if, e.g., any one of the substituents at the aromatic ring has tautomeric forms. Preferred tautomers include keto-enol tautomers.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein denotes in each case a straight-chain or branched alkyl group having usually from 1 to 4 carbon atoms, preferably from 1 to 3 carbon atoms. Preferred alkyl groups include methyl, ethyl, n-propyl, iso-propyl, n-butyl, 2-butyl, iso-butyl, tert-butyl, n-pentyl, 1-methylbutyl, 2-methylbutyl, 3-methylbutyl, and 2,2-dimethylpropyl. Methyl, ethyl, n-propyl and iso-propyl are particularly preferred.

The term "haloalkyl" as used herein denotes in each case a straight-chain or branched alkyl group having usually from 1 to 4 carbon atoms, preferably from 1 to 3 carbon atoms, especially 1 or 2 carbon atoms, wherein the hydrogen atoms of this group are partially or totally replaced with halogen atoms. Preferred haloalkyl moieties are selected from C$_1$-C$_4$-haloalkyl, more preferably from C$_1$-C$_3$-haloalkyl or C$_1$-C$_2$-haloalkyl, in particular from C$_1$-C$_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like. Trifluoromethyl is particularly preferred according to the invention.

The term "alkoxy" as used herein denotes in each case a straight-chain or branched alkyl group, which is bonded via an oxygen group, having usually from 1 to 4 carbon atoms, preferably from 1 to 3 carbon atoms, especially 1 or 2 carbon atoms. Examples of alkoxy groups are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having usually from 1 to 4 carbon atoms, preferably from 1 to 3 carbon atoms, especially 1 or 2 carbon atoms, wherein the hydrogen atoms of this group are partially or totally replaced with halogen atoms, in particular fluorine atoms. Preferred haloalkoxy moieties include C$_1$-C$_4$-haloalkoxy, in particular C$_1$-C$_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluoroethoxy, 2,2,2-trichloroethoxy, pentafluoroethoxy and the like.

The term "alkenyl" as used herein denotes in each case an at least singly unsaturated hydrocarbon radical, i.e. a hydrocarbon radical having at least one carbon-carbon double bond, having usually 2 to 4 carbon atoms, preferably 2 or 3 carbon atoms, e.g. vinyl, allyl (2-propen-1-yl), 1-propen-1-yl, 2 propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like. A preferred alkenyl group according to the invention is allyl.

The term "alkynyl" as used herein denotes in each case a hydrocarbon radical having at least one carbon-carbon triple bond and having usually 2 to 4, preferably 2 or 3 carbon atoms or 3 or 4 carbon atoms, e.g. ethynyl, propargyl (2-propyn-1-yl, also referred to as prop-2-yn-1-yl), 1-propyn-1-yl (also referred to as prop-1-yn-1-yl), 1-methylprop-2-yn-1-yl, 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like. A preferred alkynyl group according to the invention is propargyl.

The term "phenylalkyl" as used herein denotes a phenyl group, which is bonded via an alkyl group, preferably a $C_1$-$C_2$-alkyl group, in particular a methyl group (=phenylmethyl/benzyl), to the remainder of the molecule. The most preferred phenylalkyl group is benzyl.

The term "cycloalkyl" as used herein and in the cycloalkyl moieties of cycloalkoxy and cycloalkylthio denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or preferably cyclopropyl, cyclobutyl, cyclopentyl and cyclohexyl.

As has been set out above, the present invention concerns in one aspect the use of an alkoxypyrazole compound of formula I

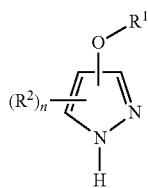

(I)

or a salt, stereoisomer, tautomer, or N-oxide thereof as a nitrification inhibitor,
wherein
  $R^1$ is $C_1$-$C_6$-alkyl, $C_3$-$C_6$-cycloalkyl, benzyl, allyl, propargyl, $CHR^aC(=O)OR^b$, $CHR^aC(=O)NR^bR^c$, or phenyl, wherein said phenyl group is unsubstituted or substituted by one or more, same or different substituents $R^x$;
  $R^2$ is halogen, $C_1$-$C_6$-alkyl, $C_1$-$C_3$-alkoxy, $C_3$-$C_6$-cycloalkyl, allyl, propargyl, benzyl, or phenyl, wherein said phenyl group is unsubstituted or substituted by one or more, same or different substituents $R^x$;
  and wherein
  $R^a$ is H, $C_1$-$C_4$-alkyl, $C_1$-$C_4$-haloalkyl, $C_3$-$C_8$-cycloalkyl, phenyl, or phenyl-$C_1$-$C_2$-alkyl;
  $R^b$ is H, $C_1$-$C_4$-alkyl, $C_1$-$C_4$-haloalkyl, $C_3$-$C_8$-cycloalkyl, phenyl, or phenyl-$C_1$-$C_2$-alkyl;
  $R^c$ is H, $C_1$-$C_4$-alkyl, $C_1$-$C_4$-haloalkyl, or phenyl;
  $R^x$ is halogen, $C_1$-$C_4$-alkyl, $C_1$-$C_4$-haloalkyl, $C_1$-$C_4$-alkoxy, or $C_1$-$C_4$-haloalkoxy;
  n is 0, 1, or 2.

It is to be understood that if n is 2, two $R^2$ substituents are present which are independently selected from the group of substituents defined above for $R^2$.

Preferred embodiments regarding the compounds of formula I, which are relevant for all aspects of the invention, are defined hereinafter.

In one embodiment of the invention, the compound of formula I

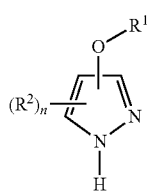

(I)

is a compound of any one of the following formulae I.1, I.2, or I.3.

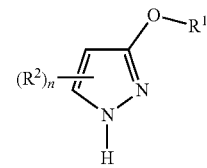

I.1

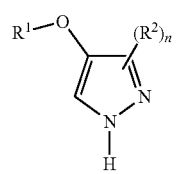

I.2

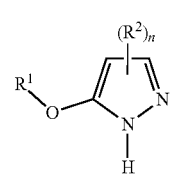

I.3

In certain preferred embodiments of the invention, the compounds of formulae I.1, I.2, or I.3 are preferably present in the form of a pyrazolium salt, preferably in the form of a pyrazolium phosphate salt. If it is referred to the compounds of formula I or substructures thereof hereinafter, the preferences also particularly refer to the compounds in the form of the pyrazolium salt, especially the pyrazolium phosphate salt.

In connection with compounds of formulae I.1, I.2, or I.3, it is preferred that n is 0 or 1, i.e. that either $R^2$ is absent or only one $R^2$ is present. If n is 1, it is in one embodiment preferred that $R^2$ is present in the 4-position of the pyrazole ring. In another embodiment, it is preferred that $R^2$ is present in the 5- or 3-position of the pyrazole ring. In certain preferred embodiments, $OR^1$ is in 3-position of the pyrazole ring, and $R^2$ is present in the 5-position of the pyrazole ring, or $OR^1$ is in 5-position of the pyrazole ring, and $R^2$ is present in the 3-position of the pyrazole ring, or mixture of these types of compounds of formulae I.1 and I.3 is present. In yet another preferred embodiment, n is 0, i.e. $R^2$ is absent.

It is to be understood that the compound of formula I may in certain embodiments be present as a mixture of a compound of formula I.1 and a compound of formula I.3. Furthermore, mixtures of formula I.2 compounds may be obtained, if at least one substituent $R^2$ is present.

Further, it is to be understood that depending on the presence or absence of the substituent $R^2$ and its position, different structures may be preferred in connection with the compounds of formula I.

Accordingly, the compound of formula I, in particular the compound of formula I.1, is in one particularly preferred embodiment a compound of any of formulae I.1(i), I.1(ii), or I.1(iii) as depicted below.

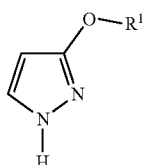

I.1(i)

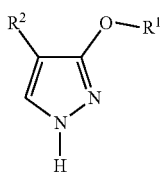

I.1(ii)

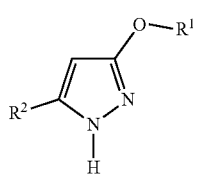

I.1(iii)

In another particularly preferred embodiment, the compound of formula I, in particular the compound of formula I.2 is a compound of any one of formulae I.2(i), I.2(ii), or I.2(iii) as depicted below.

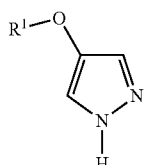

I.2(i)

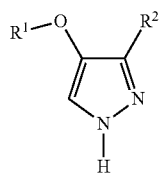

I.2(ii)

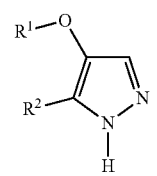

I.2(iii)

In another particularly preferred embodiment, the compound of formula I, in particular the compound of formula I.3 is a compound of any one of formulae I.3(i), I.3(ii), or I.3(iii) as depicted below.

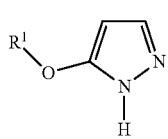

I.3(i)

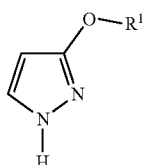

I.3(ii)

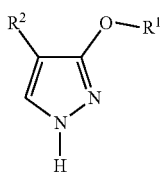

I.3(iii)

In one especially preferred embodiment, the compound of formula I is any one of the compounds of formulae I.1(ii), or I.3(iii), or a mixture thereof.

In another especially preferred embodiment, the compound of formula I is any one of the compounds of formula I.1(iii), or I.3(ii), or a mixture thereof. In this connection, it is particularly preferred that the compound of formula I is present in the form of a pyrazolium salt, especially a pyrazolium phosphate salt.

In another preferred embodiment of the invention, in the compound of formula I, and preferably in the compounds of formulae I.1, I.2, or I.3, and in particular in the compounds of formulae I.1(i), I.1(ii), or I.1(iii), or in the compounds of formulae I.2(i), I.2(ii), or I.2(iii), or in the compounds of formulae I.3(i), I.3(ii), or I.3(iii), $R^1$ is $C_1$-$C_6$-alkyl, $C_3$-$C_6$-cycloalkyl, benzyl, allyl, propargyl, $CHR^aC(=O)OR^b$, $CHR^aC(=O)NR^bR^c$, or phenyl, wherein said phenyl group is unsubstituted or substituted by one or more, same or different substituents $R^x$;

$R^2$ if present, is halogen, $C_1$-$C_6$-alkyl, $C_1$-$C_3$-alkoxy, $C_3$-$C_6$-cycloalkyl, allyl, propargyl, benzyl, or phenyl, wherein said phenyl group is unsubstituted or substituted by one or more, same or different substituents $R^x$;

wherein $R^a$, $R^b$, $R^c$ and $R^x$ are as defined above;

and especially preferably $R^1$ is allyl, $C_1$-$C_3$-alkyl, preferably $C_1$-$C_2$-alkyl;

$R^2$ if present, is $C_1$-$C_3$-alkyl or phenyl.

In certain particularly preferred embodiments, $R^1$ is allyl, $C_1$-$C_3$-alkyl, preferably $C_1$-$C_2$-alkyl, and $R^2$ is absent or $C_2$-$C_3$-alkyl or phenyl. In other particularly preferred embodiments, $R^1$ is $C_1$-alkyl, and $R^2$ is $C_1$-$C_3$-alkyl or phenyl, preferably $C_1$-alkyl.

In connection with the above preferred embodiment it is to be understood, that $OR^1$ is preferably present in the 3- or 5-position of the pyrazole ring and $R^2$, if present, is preferably present in the 5- or 3-position of the pyrazole ring. In another preferred embodiment, $R^2$, if present, is present in the 4-position of the pyrazole ring, more preferably n is 0, i.e. $R^2$ is absent. Furthermore, it is to be understood that the compounds of formula I, and preferably the compounds of formulae I.1, I.2, or I.3, and in particular the compounds of formulae I.1(i), I.1(ii), or I.1(iii), or the compounds of formulae I.2(i), I.2(ii), or I.2(iii), or the compounds of formulae I.3(i), I.3(ii), or I.3(iii), are present in the form of a pyrazolium salt, preferably in the form of a pyrazolium phosphate salt.

Thus, in connection with the compounds of formula I.1, I.2, or I.3 as defined above, it is preferred that $R^2$, if present, is $C_1$-$C_3$-alkyl or phenyl and $R^1$ is allyl, $C_1$-$C_3$-alkyl, preferably $C_1$-$C_2$-alkyl.

According to one preferred embodiment of the invention, the compound of formula I is a compound of formula I.1, wherein n is 0 or 1, and $R^2$, if present, is $C_1$-$C_3$-alkyl or phenyl and $R^1$ is allyl, $C_1$-$C_3$-alkyl, preferably $C_1$-$C_2$-alkyl.

According to one preferred embodiment of the invention, the compound of formula I is a compound of formula I.2, wherein n is 0 or 1, and $R^2$, if present, is $C_1$-$C_3$-alkyl or phenyl and $R^1$ is allyl, $C_1$-$C_3$-alkyl, preferably $C_1$-$C_2$-alkyl.

According to one preferred embodiment of the invention, the compound of formula I is a compound of formula I.3, wherein n is 0 or 1, and $R^2$, if present, is $C_1$-$C_3$-alkyl or phenyl and $R^1$ is allyl, $C_1$-$C_3$-alkyl, preferably $C_1$-$C_2$-alkyl.

According to one particularly preferred embodiment, the compound of formula I is a compound of formula I.1(i), wherein $R^1$ is allyl, $C_1$-$C_3$-alkyl, preferably $C_1$-$C_2$-alkyl.

According to one particularly preferred embodiment, the compound of formula I is a compound of any one of formulae I.1(ii), or I.1(iii), wherein $R^2$ is $C_1$-$C_3$-alkyl or phenyl, and wherein $R^1$ is allyl, $C_1$-$C_3$-alkyl, preferably $C_1$-$C_2$-alkyl.

According to one particularly preferred embodiment, the compound of formula I is a compound of formula I.2(i), wherein $R^1$ is allyl, $C_1$-$C_3$-alkyl, preferably $C_1$-$C_2$-alkyl.

According to one particularly preferred embodiment, the compound of formula I is a compound of any one of formulae I.2(ii), or I.2(iii), wherein $R^2$ is $C_1$-$C_3$-alkyl or phenyl, and wherein $R^1$ is allyl, $C_1$-$C_3$-alkyl, preferably $C_1$-$C_2$-alkyl.

According to one particularly preferred embodiment, the compound of formula I is a compound of formula I.3(i), wherein $R^1$ is allyl, $C_1$-$C_3$-alkyl, preferably $C_1$-$C_2$-alkyl.

According to one particularly preferred embodiment, the compound of formula I is a compound of any one of formulae I.3(ii), or I.3(iii), wherein $R^2$ is $C_1$-$C_3$-alkyl or phenyl, and wherein $R^1$ is allyl, $C_1$-$C_3$-alkyl, preferably $C_1$-$C_2$-alkyl.

In connection with the above particularly preferred embodiments, the meaning of $R^1$ corresponds to the meaning provided above in connection with the compounds of formula I.

In another embodiment of the invention, in the compound of formula I, and preferably in the compounds of formulae I.1, I.2, or I.3, and particularly in the compounds of formulae I.1(i), I.1(ii), or I.1(iii), or in the compounds of formulae I.2(i), I.2(ii), or I.2(iii), or in the compounds of formulae I.3(i), I.3(ii), or I.3(iii), $R^1$ is $C_1$-$C_6$-alkyl, $C_3$-$C_6$-cycloalkyl, benzyl, allyl, propargyl, $CHR^aC(=O)OR^b$, $CHR^aC(=O)NR^bR^c$, or phenyl, wherein said phenyl group is unsubstituted or substituted by one or more, same or different substituents $R^x$;

wherein $R^a$ is H, $C_1$-$C_4$-alkyl, $C_1$-$C_4$-haloalkyl, $C_3$-$C_8$-cycloalkyl, phenyl, or phenyl-$C_1$-$C_2$-alkyl;

$R^b$ is H, $C_1$-$C_4$-alkyl, $C_1$-$C_4$-haloalkyl, $C_3$-$C_8$-cycloalkyl, phenyl, or phenyl-$C_1$-$C_2$-alkyl;

$R^c$ is H, $C_1$-$C_4$-alkyl, $C_1$-$C_4$-haloalkyl, or phenyl;

$R^x$ is halogen, $C_1$-$C_4$-alkyl, $C_1$-$C_4$-haloalkyl, $C_1$-$C_4$-alkoxy, or $C_1$-$C_4$-haloalkoxy;

and preferably $R^1$ is allyl, $C_1$-$C_3$-alkyl;

more preferably $R^1$ is $C_1$-$C_2$-alkyl.

In connection with the above embodiment it is to be understood, that $OR^1$ is preferably present in the 3- or 5-position of the pyrazole ring and $R^2$, if present, is preferably present in the 5- or 3-position of the pyrazole ring. In another preferred embodiment, $R^2$, if present, is present in the 4-position of the pyrazole ring. Further, it is to be understood that $R^2$, if present, is as defined above for the compounds of formula I, preferably for the compounds of formula I.1, I.2, or I.3. In a preferred embodiment, it is to be understood, that n is 0, i.e. $R^2$ is absent. Furthermore, it is to be understood that the compounds of formulae I.1, I.2, or I.3, and particularly the compounds of formulae I.1(i), I.1(ii), or I.1(iii), or the compounds of formulae I.2(i), I.2(ii), or I.2(iii), or the compounds of formulae I.3(i), I.3(ii), or I.3(iii), are present in the form of a pyrazolium salt, preferably in the form of a pyrazolium phosphate salt.

In one preferred embodiment of the invention, in the compound of formula I $R^1$ is $CH_3$.

Such compounds are referred to as compounds of formula I.A

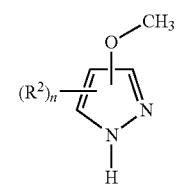

I.A

In one preferred embodiment of the invention, in the compound of formula I $R^1$ is $CH_2CH_3$.

Such compounds are referred to as compounds of formula I.B

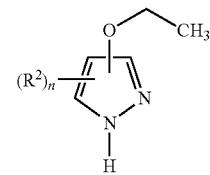

I.B

In one preferred embodiment of the invention, in the compound of formula I $R^1$ is $CH_2CH_2CH_3$.

Such compounds are referred to as compounds of formula I.C

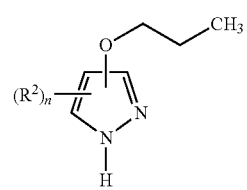

I.C

In one preferred embodiment of the invention, in the compound of formula I $R^1$ is $CH(CH_3)_2$.

Such compounds are referred to as compounds of formula I.D

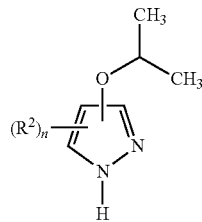

I.D

In one preferred embodiment of the invention, in the compound of formula I $R^1$ is allyl.

Such compounds are referred to as compounds of formula I.E

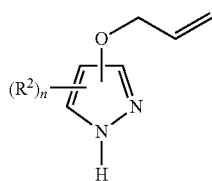

I.E

It is to be understood that the above preferences with regard to $R^2$ also apply to the above formulae I.A, I.B, I.C, I.D and I.E.

Thus, particularly preferred compounds for use according to the invention are compounds of formula I.1.A, I.1.B, I.1.C, I.1.D, or I.1.E which are depicted below.

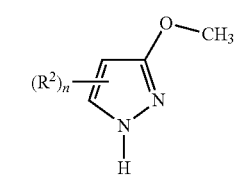

I.1.A

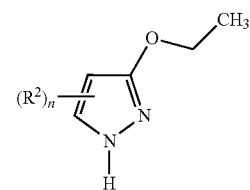

I.1.B

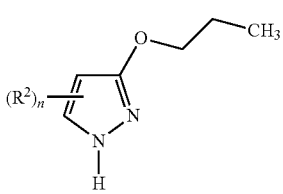

I.1.C

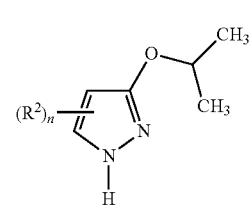

I.1.D

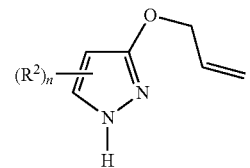

I.1.E

The meaning of $R^2$ preferably corresponds to the meaning provided above in connection with the compounds of formula I, in particular the compounds of formula I.1. Furthermore, it is preferred that n is 0 or 1. If n is 1, each of the positions at the pyrazole ring may be realized by $R^2$ as indicated in connection with the compounds of formulae I.1(ii), or I.1(iii). Furthermore, it is more preferred that n is 0, i.e. $R^2$ is absent.

Further, particularly preferred compounds for use according to the invention are compounds of formula I.2.A, I.2.B, I.2.C, I.2.D, or I.2.E which are depicted below.

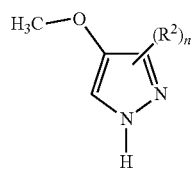

I.2.A

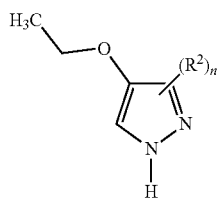

I.2.B

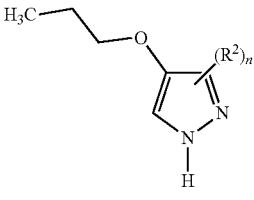

I.2.C

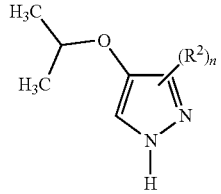

I.2.D

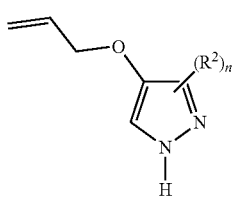

I.2.E

The meaning of $R^2$ preferably corresponds to the meaning provided above in connection with the compounds of formula I, in particular the compounds of formula I.2. Furthermore, it is preferred that n is 0 or 1. If n is 1, each of the positions at the pyrazole ring may be realized by $R^2$ as indicated in connection with the compounds of formulae I.2(ii), or I.2(iii). Furthermore, it is more preferred that n is 0, i.e. $R^2$ is absent.

Further, particularly preferred compounds for use according to the invention are compounds of formula I.3.A, I.3.B, I.3.C, I.3.D, or I.3.E which are depicted below.

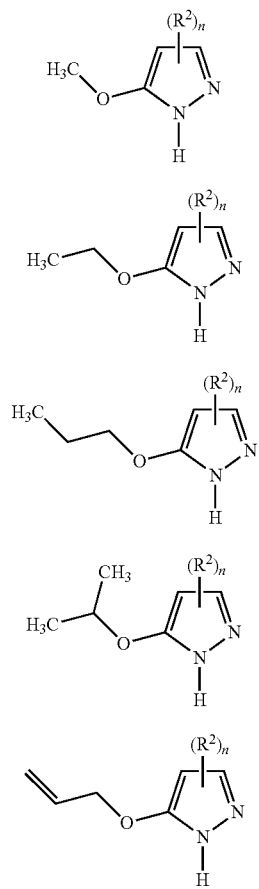

The meaning of $R^2$ preferably corresponds to the meaning provided above in connection with the compounds of formula I, in particular the compounds of formula I.3. Furthermore, it is preferred that n is 0 or 1. If n is 1, each of the positions at the pyrazole ring may be realized by $R^2$ as indicated in connection with the compounds of formulae I.3(ii), or I.3(iii). Furthermore, it is more preferred that n is 0, i.e. $R^2$ is absent.

In connection with the above preferred compounds it is to be understood that $OR^1$ is preferably present in the 3- or 5-position of the pyrazole ring and $R^2$, if present, is preferably present in the 5- or 3-position of the pyrazole ring. In another preferred embodiment, $R^2$, if present, is present in the 4-position of the pyrazole ring. Furthermore, in connection with the above preferred compounds it is to be understood that these compounds are preferably present in the form of a pyrazolium salt, preferably in the form of a pyrazolium phosphate salt.

In connection with the methods, uses, compositions, and mixtures of the invention, and in particular with a view to their use, preference is given to the compounds of formula I compiled in the tables below.

Table 1
Compounds of the formula I.1(i), wherein $R^1$ corresponds in each case to one row of Table A Table 2
Compounds of the formula I.2(i), wherein $R^1$ corresponds in each case to one row of Table A Table 3
Compounds of the formula I.3(i), wherein $R^1$ corresponds in each case to one row of Table A

TABLE A

| No. | $R^1$ |
|---|---|
| A-1 | $CH_3$ |
| A-2 | $CH_2CH_3$ |
| A-3 | $CH_2CH_2CH_3$ |
| A-4 | $CH(CH_3)_2$ |
| A-5 | allyl |

In connection with the compounds according to Tables 1, 2, and 3, it is preferred that the compounds are present in the form of a pyrazolium salt, more preferably in the form of a pyrazolium phosphate salt.

Table 4
Compounds of the formula I.1(ii), wherein $R^1$ and $R^2$ correspond in each case to one row of Table B Table 5
Compounds of the formula I.1(iii), wherein $R^1$ and $R^2$ correspond in each case to one row of Table B Table 6
Compounds of the formula I.2(ii), wherein $R^1$ and $R^2$ correspond in each case to one row of Table B Table 7
Compounds of the formula I.2(iii), wherein $R^1$ and $R^2$ correspond in each case to one row of Table B Table 8
Compounds of the formula I.3(ii), wherein $R^1$ and $R^2$ correspond in each case to one row of Table B Table 9
Compounds of the formula I.3(iii), wherein $R^1$ and $R^2$ correspond in each case to one row of Table B

TABLE B

| No. | $R^2$ | $R^1$ |
|---|---|---|
| B-1 | $CH_3$ | $CH_3$ |
| B-2 | $CH_2CH_3$ | $CH_3$ |
| B-3 | $CH_2CH_2CH_3$ | $CH_3$ |
| B-4 | $CH(CH_3)_2$ | $CH_3$ |
| B-5 | phenyl | $CH_3$ |
| B-6 | $CH_3$ | $CH_2CH_3$ |
| B-7 | $CH_2CH_3$ | $CH_2CH_3$ |
| B-8 | $CH_2CH_2CH_3$ | $CH_2CH_3$ |
| B-9 | $CH(CH_3)_2$ | $CH_2CH_3$ |
| B-10 | phenyl | $CH_2CH_3$ |
| B-11 | $CH_3$ | $CH_2CH_2CH_3$ |
| B-12 | $CH_2CH_3$ | $CH_2CH_2CH_3$ |
| B-13 | $CH_2CH_2CH_3$ | $CH_2CH_2CH_3$ |
| B-14 | $CH(CH_3)_2$ | $CH_2CH_2CH_3$ |
| B-15 | phenyl | $CH_2CH_2CH_3$ |
| B-16 | $CH_3$ | $CH(CH_3)_2$ |
| B-17 | $CH_2CH_3$ | $CH(CH_3)_2$ |
| B-18 | $CH_2CH_2CH_3$ | $CH(CH_3)_2$ |
| B-19 | $CH(CH_3)_2$ | $CH(CH_3)_2$ |
| B-20 | phenyl | $CH(CH_3)_2$ |
| B-21 | $CH_3$ | allyl |
| B-22 | $CH_2CH_3$ | allyl |
| B-23 | $CH_2CH_2CH_3$ | allyl |
| B-24 | $CH(CH_3)_2$ | allyl |
| B-25 | phenyl | allyl |

In connection with the compounds according to Tables 1, 2, and 3, it is preferred that the compounds are present in the form of a pyrazolium salt, more preferably in the form of a pyrazolium phosphate salt.

It has been found that the compounds as defined in the above tables are not only advantageous in terms of reducing nitrification, but also in view of the fact that they have advantageous properties, e.g., in terms of their low volatility and/or their environmental safety. Furthermore, the compounds according to the present invention can cost-efficiently be prepared.

It is to be understood that also combinations of the above compounds may be used as nitrification inhibitors according to the present invention, in particular combinations of compounds, which are obtained as isomer mixtures after the N-substituent has been introduced as outlined above.

In connection with the methods, uses, compositions, and mixtures of the invention, and in particular with a view to their use, the following preferred embodiments are additionally relevant:

In a central aspect the present invention thus relates to the use of a compound of formula I as defined herein as a nitrification inhibitor, or to the use of a composition comprising said compound of formula I as defined herein for reducing nitrification. The compound of formula I or derivatives or salts thereof as defined herein, in particular the compounds of formula I and/or salts or suitable derivatives thereof, as well as compositions comprising said compound of formula I, or agrochemical mixtures comprising said compound of formula I may be used for reducing nitrification.

The use may be based on the application of the nitrification inhibitor, the composition or the agrochemical mixture as defined herein to a plant growing on soil and/or the locus where the plant is growing or is intended to grow, or the use may be based on the application of the nitrification inhibitor, the composition or the agrochemical mixture as defined herein to soil where a plant is growing or is intended to grow or to soil substituents. In specific embodiments, the nitrification inhibitor may be used for reducing nitrification in the absence of plants, e.g. as preparatory activity for subsequent agricultural activity, or for reducing nitrification in other technical areas, which are not related to agriculture, e.g. for environmental, water protection, energy production or similar purposes. In specific embodiments, the nitrification inhibitor, or a composition comprising said nitrification inhibitor according to the present invention may be used for the reduction of nitrification in sewage, slurry, manure or dung of animals, e.g. swine or bovine feces. For example, the nitrification inhibitor, or a composition comprising said nitrification inhibitor according to the present invention may be used for the reduction of nitrification in sewage plants, biogas plants, cowsheds, liquid manure tanks or containers etc. Furthermore, the nitrification inhibitor, or a composition comprising said nitrification inhibitor may be used in exhaust air systems, preferably in exhaust air systems of stables or cowsheds. The present invention therefore also relates to the use of compounds of formula I for treating exhaust air, preferably the exhaust air of stables and cowsheds. In further embodiments, the nitrification inhibitor, or a composition comprising said nitrification inhibitor according to the present invention may be used for the reduction of nitrification in situ in animals, e.g. in productive livestock. Accordingly, the nitrification inhibitor, or a composition comprising said nitrification inhibitor according to the present invention may be fed to an animal, e.g. a mammal, for instance together with suitable feed and thereby lead to a reduction of nitrification in the gastrointestinal tract of the animals, which in turn is resulting in reduction of emissions from the gastrointestinal tract. This activity, i.e. the feeding of nitrification inhibitor, or a composition comprising said nitrification inhibitor according to the present invention may be repeated one to several times, e.g. each $2^{nd}$, $3^{rd}$, $4^{th}$, $5^{th}$, $6^{th}$, $7^{th}$ day, or each week, 2 weeks, 3 weeks, or month, 2 months etc.

The use may further include the application of a nitrification inhibitor or derivatives or salts thereof as defined herein above, in particular compounds of formula I and/or salts or suitable derivatives thereof, as well as compositions comprising said nitrification inhibitor, or agrochemical mixtures comprising said nitrification inhibitor as defined herein above to environments, areas or zones, where nitrification takes place or is assumed or expected to take place. Such environments, areas or zones may not comprise plants or soil. For example, the inhibitors may be used for nitrification inhibition in laboratory environments, e.g. based on enzymatic reactions or the like. Also envisaged is the use in green houses or similar indoor facilities.

The term "reducing nitrification" or "reduction of nitrification" as used herein refers to a slowing down or stopping of nitrification processes, e.g. by retarding or eliminating the natural transformation of ammonium into nitrate. Such reduction may be a complete or partial elimination of nitrification at the plant or locus where the inhibitor or composition comprising said inhibitor is applied. For example, a partial elimination may result in a residual nitrification on or in the plant, or in or on the soil or soil substituents where a plant grows or is intended to grow of about 90% to 1%, e.g. 90%, 85%, 80%, 70%, 60%, 50%, 40%, 30%, 20%, 10% or less than 10%, e.g. 5% or less than 5% in comparison to a control situation where the nitrification inhibitor is not used. In certain embodiments, a partial elimination may result in a residual nitrification on or in the plant or in or on the soil or soil substituents where a plant grows or is intended to grow of below 1%, e.g. at 0.5%, 0.1% or less in comparison to a control situation where the nitrification inhibitor is not used.

The use of a nitrification inhibitor as defined herein above, or of a composition as defined herein for reducing nitrification may be a single use, or it may be a repeated use. As single use, the nitrification inhibitor or corresponding compositions may be provided to their target sites, e.g. soil or loci, or objects, e.g. plants, only once in a physiologically relevant time interval, e.g. once a year, or once every 2 to 5 years, or once during the lifetime of a plant. In other embodiments, the use may be repeated at least once per time period, e.g. the nitrification inhibitor as defined herein above, or a composition as defined herein may be used for reducing nitrification at their target sites or objects two times within a time interval of days, weeks or months. The term "at least once" as used in the context of a use of the nitrification inhibitor means that the inhibitor may be used two times, or several times, i.e. that a repetition or multiple repetitions of an application or treatment with a nitrification inhibitor may be envisaged. Such a repetition may be a 2 times, 3 times, 4 times, 5 times, 6 times, 7 times, 8 times, 9 times, 10 times or more frequent repetition of the use.

The nitrification inhibitor according to the present invention may be used in any suitable form. For example, it may be used as coated or uncoated granule, in liquid or semi-liquid form, as sprayable entity, or in irrigation approaches etc. In specific embodiments, the nitrification inhibitor as defined herein may be applied or used as such, i.e. without formulations, fertilizer, additional water, coatings, or any further ingredient.

The term "irrigation" as used herein refers to the watering of plants or loci or soils or soil substituents where a plant grows or is intended to grow, wherein said watering includes the provision of the nitrification inhibitor according to the present invention together with water.

In a further aspect the invention relates to a composition for reducing nitrification comprising at least one nitrification inhibitor wherein said nitrification inhibitor is a compound of formula I or a derivative as defined herein above; and at least one carrier.

The term "composition for reducing nitrification" as used herein refers to a composition which is suitable, e.g. comprises effective concentrations and amounts of ingredients such as nitrification inhibitors, in particular compounds of formula I or derivatives as defined herein, for reducing nitrification in any context or environment in which nitrification may occur. In one embodiment, the nitrification may be reduced in or on or at the locus of a plant. Typically, the nitrification may be reduced in the root zone of a plant. However, the area in which such reduction of nitrification may occur is not limited to the plants and their environment, but may also include any other habitat of nitrifying bacteria or any site at which nitrifying enzymatic activities can be found or can function in a general manner, e.g. sewage plants, biogas plants, animal effluents from productive livestock, e.g. cows, pigs etc. "Effective amounts" or "effective concentrations" of nitrification inhibitors as defined herein may be determined according to suitable in vitro and in vivo testings known to the skilled person. These amounts and concentrations may be adjusted to the locus, plant, soil, climate conditions or any other suitable parameter which may have an influence on nitrification processes.

A "carrier" as used herein is a substance or composition which facilitates the delivery and/or release of the ingredients to the place or locus of destination. The term includes, for instance, agrochemical carriers which facilitate the delivery and/or release of agrochemicals in their field of use, in particular on or into plants.

Examples of suitable carriers include solid carriers such as phytogels, or hydrogels, or mineral earths e.g. silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g. an solid or liquid ammonium-containing inorganic fertilizer such as an NPK fertilizer, ammonium nitrate, calcium ammonium nitrate, ammonium sulfate nitrate, ammonium sulfate or ammonium phosphate; an solid or liquid organic fertilizer such as liquid manure, semi-liquid manure, stable manure, biogas manure and straw manure, worm castings, compost, seaweed or guano, or an urea-containing fertilizer such as urea, formaldehyde urea, anhydrous ammonium, urea ammonium nitrate (UAN) solution, urea sulphur, stabilized urea, urea based NPK-fertilizers, or urea ammonium sulfate, and products of vegetable origin, such as cereal meal, tree bark meal, wood meal and nutshell meal, cellulose powders and other solid carriers. Further suitable examples of carriers include fumed silica or precipitated silica, which may, for instance, be used in solid formulations as flow aid, anti-caking aid, milling aid and as carrier for liquid active ingredients. Additional examples of suitable carriers are microparticles, for instance microparticles which stick to plant leaves and release their content over a certain period of time. In specific embodiments, agrochemical carriers such as composite gel microparticles that can be used to deliver plant-protection active principles, e.g. as described in U.S. Pat. No. 6,180,141; or compositions comprising at least one phytoactive compound and an encapsulating adjuvant, wherein the adjuvant comprises a fungal cell or a fragment thereof, e.g. as described in WO 2005/102045; or carrier granules, coated with a lipophilic tackifier on the surface, wherein the carrier granule adheres to the surface of plants, grasses and weeds, e.g. as disclosed in US 2007/0280981 may be used. In further specific embodiments, such carriers may include specific, strongly binding molecule which assure that the carrier sticks to the plant, the seed, and/or loci where the plant is growing or is intended to grow, till its content is completely delivered. For instance, the carrier may be or comprise cellulose binding domains (CBDs) have been described as useful agents for attachment of molecular species to cellulose (see U.S. Pat. No. 6,124,117); or direct fusions between a CBD and an enzyme; or a multifunctional fusion protein which may be used for delivery of encapsulated agents, wherein the multifunctional fusion proteins may consist of a first binding domain which is a carbohydrate binding domain and a second binding domain, wherein either the first binding domain or the second binding domain can bind to a microparticle (see also WO 03/031477). Further suitable examples of carriers include bifunctional fusion proteins consisting of a CBD and an anti-RR6 antibody fragment binding to a microparticle, which complex may be deposited onto treads or cut grass (see also WO 03/031477). In another specific embodiment the carrier may be active ingredient carrier granules that adhere to e.g. the surface of plants, grasses, weeds, seeds, and/or loci where the plant is growing or is intended to grow etc. using a moisture-active coating, for instance including gum arabic, guar gum, gum karaya, gum tragacanth and locust bean gum. Upon application of the inventive granule onto a plant surface, water from precipitation, irrigation, dew, co-application with the granules from special application equipment, or guttation water from the plant itself may provide sufficient moisture for adherence of the granule to the plant surface (see also US 2007/0280981).

In another specific embodiment the carrier, e.g. an agrochemical carrier, may be or comprise polyaminoacids. Polyaminoacids may be obtained according to any suitable process, e.g. by polymerization of single or multiple amino acids such as glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine, histidine and/or ornithine. Polyaminoacids may be combined with a nitrification inhibitor according to the present invention and, in certain embodiments, also with further carriers as mentioned herein above, or other nitrification inhibitors as mentioned herein in any suitable ratio. For example, Polyaminoacids may be combined with a nitrification inhibitor according to the present invention in a ratio of 1 to 10 (polyaminoacids) vs. 0.5 to 2 (nitrification inhibitor according to the present invention).

The composition for reducing nitrification comprising at least one nitrification inhibitor as defined herein may further comprise additional ingredients, for example at least one pesticidal compound. For example, the composition may additionally comprise at least one herbicidal compound and/or at least one fungicidal compound and/or at least one insecticidal compound and/or at least one nematicide and/or at least one biopesticide and/or at least one biostimulant.

In further embodiments, the composition may, in addition to the above indicated ingredients, in particular in addition to the nitrification inhibitor of the compound of formula I, further comprise one or more alternative or additional nitrification inhibitors. Examples of envisaged alternative or additional nitrification inhibitors are linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST), ammoniumthiosulfate (ATU), 3-methylpyrazol (3-MP), 3,5-dimethylpyrazole (DMP), 1,2,4-triazol thiourea (TU), N-(1-H-pyrazolyl-methyl)acetamides such as N-((3(5)-methyl-1H-pyrazole-1-yl)methyl)acetamide, and N-(1-H-pyrazolyl-methyl) formamides such as N-((3(5)-methyl-1H-pyrazole-1-yl) methyl formamide, N-(4-chloro-3(5)-methyl-pyrazole-1-ylmethyl)-formamide, N-(3(5),4-dimethyl-pyrazole-1-ylmethyl)-formamide, neem, products based on ingredients of neem, cyan amide, melamine, zeolite powder, catechol, benzoquinone, sodium terta board, zinc sulfate.

In a preferred embodiment, the composition according to the present invention may comprise a combination of the nitrification inhibitor of the compound of formula I and 2-chloro-6-(trichloromethyl)-pyridine (nitrapyrin or N-serve).

In a further preferred embodiment, the composition according to the present invention may comprise a combination of the nitrification inhibitor of the compound of formula I and 5-ethoxy-3-trichloromethyl-1,2,4-thiodiazole (terrazole, etridiazole).

In a further preferred embodiment, the composition according to the present invention may comprise a combination of the nitrification inhibitor of the compound of formula I and dicyandiamide (DCD, DIDIN).

In a further preferred embodiment, the composition according to the present invention may comprise a combination of the nitrification inhibitor of the compound of formula I and 3,4-dimethyl pyrazole phosphate (DMPP, ENTEC).

In a further preferred embodiment, the composition according to the present invention may comprise a combination of the nitrification inhibitor of the compound of formula I and 2-amino-4-chloro-6-methylpyrimidine (AM).

In a further preferred embodiment, the composition according to the present invention may comprise a combination of the nitrification inhibitor of the compound of formula I and 2-mercapto-benzothiazole (MBT).

In a further preferred embodiment, the composition according to the present invention may comprise a combination of the nitrification inhibitor of the compound of formula I and 2-sulfanilamidothiazole (ST).

In a further preferred embodiment, the composition according to the present invention may comprise a combination of the nitrification inhibitor of the compound of formula I and ammoniumthiosulfate (ATU).

In a further preferred embodiment, the composition according to the present invention may comprise a combination of the nitrification inhibitor of the compound of formula I and 3-methylpyrazol (3-MP).

In a further preferred embodiment, the composition according to the present invention may comprise a combination of the nitrification inhibitor of the compound of formula I and 3,5-dimethylpyrazole (DMP).

In a further preferred embodiment, the composition according to the present invention may comprise a combination of the nitrification inhibitor of the compound of formula I and 1,2,4-triazol.

In a further preferred embodiment, the composition according to the present invention may comprise a combination of the nitrification inhibitor of the compound of formula I and thiourea (TU).

In yet another preferred embodiment, the composition according to the present invention may comprise a combination of the nitrification inhibitor of the compound of formula I and linoleic acid In yet another preferred embodiment, the composition according to the present invention may comprise a combination of the nitrification inhibitor of the compound of formula I and alpha-linolenic acid.

In yet another preferred embodiment, the composition according to the present invention may comprise a combination of the nitrification inhibitor of the compound of formula I and methyl p-coumarate.

In yet another preferred embodiment, the composition according to the present invention may comprise a combination of the nitrification inhibitor of the compound of formula I and methyl 3-(4-hydroxyphenyl) propionate (MHPP).

In yet another preferred embodiment, the composition according to the present invention may comprise a combination of the nitrification inhibitor of the compound of formula I and methyl ferulate.

In yet another preferred embodiment, the composition according to the present invention may comprise a combination of the nitrification inhibitor of the compound of formula I and Karanjin.

In yet another preferred embodiment, the composition according to the present invention may comprise a combination of the nitrification inhibitor of the compound of formula I and brachialacton.

In yet another preferred embodiment, the composition according to the present invention may comprise a combination of the nitrification inhibitor of the compound of formula I and p-benzoquinone sorgoleone.

In yet another preferred embodiment, the composition according to the present invention may comprise a combination of the nitrification inhibitor of the compound of formula I and 4-amino-1,2,4-triazole hydrochloride (ATC).

In yet another preferred embodiment, the composition according to the present invention may comprise a combination of the nitrification inhibitor of the compound of formula I and 1-amido-2-thiourea (ASU).

In yet another preferred embodiment, the composition according to the present invention may comprise a combination of the nitrification inhibitor of the compound of formula I and N-((3(5)-methyl-1H-pyrazole-1-yl)methyl)acetamide.

In yet another preferred embodiment, the composition according to the present invention may comprise a combination of the nitrification inhibitor of the compound of formula I and N-((3(5)-methyl-1H-pyrazole-1-yl)methyl formamide.

In yet another preferred embodiment, the composition according to the present invention may comprise a combination of the nitrification inhibitor of the compound of formula I and N-(4-chloro-3(5)-methyl-pyrazole-1-ylmethyl)-formamide.

In yet another preferred embodiment, the composition according to the present invention may comprise a combination of the nitrification inhibitor of the compound of formula I and N-(3(5),4-dimethyl-pyrazole-1-ylmethyl)-formamide.

In yet another preferred embodiment, the composition according to the present invention may comprise a combination of the nitrification inhibitor of the compound of formula I and neem or products based on ingredients of neem.

In yet another preferred embodiment, the composition according to the present invention may comprise a combination of the nitrification inhibitor of the compound of formula I and cyanamide.

In yet another preferred embodiment, the composition according to the present invention may comprise a combination of the nitrification inhibitor of the compound of formula I and melamine.

In yet another preferred embodiment, the composition according to the present invention may comprise a combination of the nitrification inhibitor of the compound of formula I and zeolite powder.

In yet another preferred embodiment, the composition according to the present invention may comprise a combination of the nitrification inhibitor of the compound of formula I and batechol.

In yet another preferred embodiment, the composition according to the present invention may comprise a combination of the nitrification inhibitor of the compound of formula I and benzoquinone.

In yet another preferred embodiment, the composition according to the present invention may comprise a combination of the nitrification inhibitor of the compound of formula I and sodium terat borate.

In yet another preferred embodiment, the composition according to the present invention may comprise a combination of the nitrification inhibitor of the compound of formula I and zinc sulfate.

In further embodiments, the composition according to the present invention may comprise a combination of the nitrification inhibitor of the compound of formula I and two entities selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST), ammoniumthiosulfate (ATU), 3-methylpyrazol (3-MP), 3,5-dimethylpyrazole (DMP), 1,2,4-triazol and thiourea (TU), N-(1-H-pyrazolyl-methyl)acetamides such as N-((3(5)-methyl-1H-pyrazole-1-yl)methyl)acetamide, and N-(1-H-pyrazolyl-methyl)formamides such as N-((3(5)-methyl-1H-pyrazole-1-yl)methyl formamide, N-(4-chloro-3(5)-methyl-pyrazole-1-ylmethyl)-formamide, or N-(3(5),4-dimethyl-pyrazole-1-ylmethyl)-formamide neem, products based on ingredients of neem, cyan amide, melamine, zeolite powder, catechol, benzoquinone, sodium terta board, zinc sulfate.

In yet another group of embodiments, the composition according to the present invention may comprise a combination of the nitrification inhibitor of the compound of formula I and three, four or more entities selected from the group comprising: linoleic acid, alpha-linolenic acid, methyl p-coumarate, methyl ferulate, methyl 3-(4-hydroxyphenyl) propionate (MHPP), Karanjin, brachialacton, p-benzoquinone sorgoleone, 2-chloro-6-(trichloromethyl)-pyridine (nitrapyrin or N-serve), dicyandiamide (DCD, DIDIN), 3,4-dimethyl pyrazole phosphate (DMPP, ENTEC), 4-amino-1,2,4-triazole hydrochloride (ATC), 1-amido-2-thiourea (ASU), 2-amino-4-chloro-6-methylpyrimidine (AM), 2-mercapto-benzothiazole (MBT), 5-ethoxy-3-trichloromethyl-1,2,4-thiodiazole (terrazole, etridiazole), 2-sulfanilamidothiazole (ST) ammoniumthiosulfate (ATU), 3-methylpyrazol (3-MP), 3,5-dimethylpyrazole (DMP), 1,2,4-triazol and thiourea (TU), N-(1-H-pyrazolyl-methyl)acetamides such as N-((3(5)-methyl-1H-pyrazole-1-yl)methyl)acetamide, and N-(1-H-pyrazolyl-methyl)formamides such as N-((3(5)-methyl-1H-pyrazole-1-yl)methyl formamide, N-(4-chloro-3(5)-methyl-pyrazole-1-ylmethyl)-formamide, or N-(3(5),4-dimethyl-pyrazole-1-ylmethyl)-formamide neem, products based on ingredients of neem, cyan amide, melamine, zeolite powder, catechol, benzoquinone, sodium terta board, zinc sulfate. In further embodiments, the composition may, in addition to the above indicated ingredients, in particular in addition to the nitrification inhibitor of the compound of formula I, further comprise one or more urease inhibitors. Examples of envisaged urease inhibitors include N-(n-butyl) thiophosphoric acid triamide (NBPT, Agrotain), N-(n-propyl) thiophosphoric acid triamide (NPPT), 2-nitrophenyl phosphoric triamide (2-NPT), further NXPTs known to the skilled person, phenylphosphorodiamidate (PPD/PPDA), hydroquinone, ammonium thiosulfate, and mixtures of NBPT and NPPT (see e.g. U.S. Pat. No. 8,075,659). Such mixtures of NBPT and NPPT may comprise NBPT in amounts of from 40 to 95% wt.-% and preferably of 60 to 80% wt.-% based on the total amount of active substances. Such mixtures are marketed as LIMUS, which is a composition comprising about 16.9 wt.-% NBPT and about 5.6 wt.-% NPPT and about 77.5 wt.-% of other ingredients including solvents and adjuvants.

In a preferred embodiment, the composition according to the present invention may comprise a combination of the nitrification inhibitor of the compound of formula I and N-(n-butyl) thiophosphoric acid triamide (NBPT, Agrotain).

In a further preferred embodiment, the composition according to the present invention may comprise a combination of the nitrification inhibitor of the compound of formula I and phenylphosphorodiamidate (PPD/PPDA).

In a further preferred embodiment, the composition according to the present invention may comprise a combination of the nitrification inhibitor of the compound of formula I and N-(n-propyl) thiophosphoric acid triamide (NPPT).

In a further preferred embodiment, the composition according to the present invention may comprise a combination of the nitrification inhibitor of the compound of formula I and 2-nitrophenyl phosphoric triamide (2-NPT).

In a further preferred embodiment, the composition according to the present invention may comprise a combination of the nitrification inhibitor of the compound of formula I and hydroquinone.

In a further preferred embodiment, the composition according to the present invention may comprise a combination of the nitrification inhibitor of the compound of formula I and ammonium thiosulfate.

In yet another preferred embodiment, the composition according to the present invention may comprise a combination of the nitrification inhibitor of the compound of formula I and neem.

In yet another preferred embodiment, the composition according to the present invention may comprise a combination of the nitrification inhibitor of the compound of formula I and cyanamide.

In yet another preferred embodiment, the composition according to the present invention may comprise a combination of the nitrification inhibitor of the compound of formula I and melamine. In a further preferred embodiment, the composition according to the present invention may comprise a combination of the nitrification inhibitor of the compound of formula I and a mixture of NBPT and NPPT such as LIMUS.

In further embodiments, the composition according to the present invention may comprise a combination of the nitrification inhibitor of the compound of formula I and two or more entities selected from the group comprising: N-(n-butyl) thiophosphoric acid triamide (NBPT, Agrotain), N-(n-propyl) thiophosphoric acid triamide (NPPT), 2-nitrophenyl phosphoric triamide (2-NPT), further NXPTs known to the skilled person, phenylphosphorodiamidate (PPD/PPDA), hydroquinone, ammonium thiosulfate, and LIMUS.

In further embodiments, the composition may, in addition to one, more or all of the above indicated ingredients, in particular in addition to the nitrification inhibitor of the compound of formula I, further comprise one or more plant growth regulators. Examples of envisaged plant growth regulators are antiauxins, auxins, cytokinins, defoliants, ethylene modulators, ethylene releasers, gibberellins, growth inhibitors, morphactins, growth retardants, growth stimulators, and further unclassified plant growth regulators.

Suitable examples of antiauxins to be used in a composition according to the present invention are clofibric acid or 2,3,5-tri-iodobenzoic acid.

Suitable examples of auxins to be used in a composition according to the present invention are 4-CPA, 2,4-D, 2,4-DB, 2,4-DEP, dichlorprop, fenoprop, IAA (indole-3-acetic acid), IBA, naphthaleneacetamide, alpha-naphthaleneacetic acid, 1-naphthol, naphthoxyacetic acid, potassium naphthenate, sodium naphthenate or 2,4,5-T.

Suitable examples of cytokinins to be used in a composition according to the present invention are 2iP, 6-Benzylaminopurine (6-BA) (=N-6 Benzyladenine), 2,6-Dimethylpuridine (N-Oxide-2,6-Lultidine), 2,6-Dimethylpyridine, kinetin, or zeatin.

Suitable examples of defoliants to be used in a composition according to the present invention are calcium cyanamide, dimethipin, endothal, merphos, metoxuron, pentachlorophenol, thidiazuron, tribufos, or tributyl phosphorotrithioate.

Suitable examples of ethylene modulators to be used in a composition according to the present invention are aviglycine, 1-methylcyclopropene (1-MCP)

Prohexadione (prohexadione calcium), or trinexapac (Trinexapac-ethyl).

Suitable examples of ethylene releasers to be used in a composition according to the present invention are ACC, etacelasil, ethephon, or glyoxime.

Suitable examples of gibberellins to be used in a composition according to the present invention are gibberelline or gibberellic acid.

Suitable examples of growth inhibitors to be used in a composition according to the present invention are abscisic acid, S-abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat (mepiquat chloride, mepiquat pentaborate), piproctanyl, prohydrojasmon, propham, or 2,3,5-tri-iodobenzoic acid.

Suitable examples of morphactins to be used in a composition according to the present invention are chlorfluren, chlorflurenol, dichlorflurenol, or flurenol Suitable examples of growth retardants to be used in a composition according to the present invention are chlormequat (chlormequat chloride), daminozide, flurprimidol, mefluidide, paclobutrazol, tetcyclacis, uniconazole, metconazol.

Suitable examples of growth stimulators to be used in a composition according to the present invention are brassinolide, forchlorfenuron, or hymexazol.

Suitable examples of further unclassified plant growth regulators to be used in a composition according to the present invention are amidochlor, benzofluor, buminafos, carvone, choline chloride, ciobutide, clofencet, cloxyfonac, cyanamide, cyclanilide, cycloheximide, cyprosulfamide, epocholeone, ethychlozate, ethylene, fenridazon, fluprimidol, fluthiacet, heptopargil, holosulf, inabenfide, karetazan, lead arsenate, methasulfocarb, pydanon, sintofen, diflufenzopyr or triapenthenol.

In a preferred embodiment, the composition according to the present invention may comprise a combination of the nitrification inhibitor of the compound of formula I and at least one compound selected from the group comprising: abscisic acid, amidochlor, ancymidol, 6-benzylaminopurine (=N-6 benzyladenine), brassinolide, butralin, chlormequat (chlormequat chloride), choline chloride, cyclanilide, daminozide, diflufenzopyr, dikegulac, dimethipin, 2,6-dimethylpyridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), 1-methylcyclopropene (1-MCP), naphthaleneacetic acid, N-6 benzyladenine, paclobutrazol, prohexadione (prohexadione calcium), prohydrojasmon, thidiazuron, triapenthenol, tributyl phosphorotrithioate, 2,3,5-tri-iodobenzoic acid, trinexapac-ethyl, and uniconazole.

In a preferred embodiment, the composition according to the present invention may comprise a combination of the nitrification inhibitor of the compound of formula I and clofibric acid.

In a further preferred embodiment, the composition according to the present invention may comprise a combination of the nitrification inhibitor of the compound of formula I and 2,3,5-tri-iodobenzoic acid.

In a further preferred embodiment, the composition according to the present invention may comprise a combination of the nitrification inhibitor of the compound of formula I and 4-CPA.

In a further preferred embodiment, the composition according to the present invention may comprise a combination of the nitrification inhibitor of the compound of formula I and 2,4-D.

In a further preferred embodiment, the composition according to the present invention may comprise a combination of the nitrification inhibitor of the compound of formula I and 2,4-DB.

In a further preferred embodiment, the composition according to the present invention may comprise a combination of the nitrification inhibitor of the compound of formula I and 2,4-DEP.

In a further preferred embodiment, the composition according to the present invention may comprise a combination of the nitrification inhibitor of the compound of formula I and dichlorprop.

In a further preferred embodiment, the composition according to the present invention may comprise a combination of the nitrification inhibitor of the compound of formula I and fenoprop.

In a further preferred embodiment, the composition according to the present invention may comprise a combination of the nitrification inhibitor of the compound of formula I and IAA (indole-3-acetic acid).

In a further preferred embodiment, the composition according to the present invention may comprise a combination of the nitrification inhibitor of the compound of formula I and IBA.

In a further preferred embodiment, the composition according to the present invention may comprise a combination of the nitrification inhibitor of the compound of formula I and naphthaleneacetamide.

In a further preferred embodiment, the composition according to the present invention may comprise a combination of the nitrification inhibitor of the compound of formula I and alpha-naphthaleneacetic acid.

In a further preferred embodiment, the composition according to the present invention may comprise a combination of the nitrification inhibitor of the compound of formula I and 1-naphthol.

In a further preferred embodiment, the composition according to the present invention may comprise a combination of the nitrification inhibitor of the compound of formula I and naphthoxyacetic acid.

In a further preferred embodiment, the composition according to the present invention may comprise a combination of the nitrification inhibitor of the compound of formula I and potassium naphthenate.

In a further preferred embodiment, the composition according to the present invention may comprise a combination of the nitrification inhibitor of the compound of formula I and sodium naphthenate.

In a further preferred embodiment, the composition according to the present invention may comprise a combination of the nitrification inhibitor of the compound of formula I and 2,4,5-T.

In a further preferred embodiment, the composition according to the present invention may comprise a combination of the nitrification inhibitor of the compound of formula I and 2iP.

In a further preferred embodiment, the composition according to the present invention may comprise a combination of the nitrification inhibitor of the compound of formula I and 6-Benzylaminopurine (6-BA) (=N-6 Benzyladenine).

In a further preferred embodiment, the composition according to the present invention may comprise a combination of the nitrification inhibitor of the compound of formula I and 2,6-Dimethylpuridine (N-Oxide-2,6-Lultidine).

In a further preferred embodiment, the composition according to the present invention may comprise a combination of the nitrification inhibitor of the compound of formula I and zeatin.

In a further preferred embodiment, the composition according to the present invention may comprise a combination of the nitrification inhibitor of the compound of formula I and kinetin.

In a further preferred embodiment, the composition according to the present invention may comprise a combination of the nitrification inhibitor of the compound of formula I and calcium cyanamide.

In a further preferred embodiment, the composition according to the present invention may comprise a combination of the nitrification inhibitor of the compound of formula I and dimethipin.

In a further preferred embodiment, the composition according to the present invention may comprise a combination of the nitrification inhibitor of the compound of formula I and endothal.

In a further preferred embodiment, the composition according to the present invention may comprise a combination of the nitrification inhibitor of the compound of formula I and merphos.

In a further preferred embodiment, the composition according to the present invention may comprise a combination of the nitrification inhibitor of the compound of formula I and metoxuron.

In a further preferred embodiment, the composition according to the present invention may comprise a combination of the nitrification inhibitor of the compound of formula I and pentachlorophenol.

In a further preferred embodiment, the composition according to the present invention may comprise a combination of the nitrification inhibitor of the compound of formula I and thidiazuron.

In a further preferred embodiment, the composition according to the present invention may comprise a combination of the nitrification inhibitor of the compound of formula I and tribufos.

In a further preferred embodiment, the composition according to the present invention may comprise a combination of the nitrification inhibitor of the compound of formula I and tributyl phosphorotrithioate.

In a further preferred embodiment, the composition according to the present invention may comprise a combination of the nitrification inhibitor of the compound of formula I and aviglycine.

In a further preferred embodiment, the composition according to the present invention may comprise a combination of the nitrification inhibitor of the compound of formula I and 1-methylcyclopropene.

A composition as defined herein, in particular a composition comprising a nitrification inhibitor as defined herein and a plant growth regulator as defined herein, may be used for the increase of plant health.

The term "plant health" as used herein is intended to mean a condition of the plant which is determined by several aspects alone or in combination with each other. One indicator (indicator 1) for the condition of the plant is the crop yield. "Crop" and "fruit" are to be understood as any plant product which is further utilized after harvesting, e.g. fruits in the proper sense, vegetables, nuts, grains, seeds, wood (e.g. in the case of silviculture plants), flowers (e.g. in the case of gardening plants, ornamentals) etc., that is anything of economic value that is produced by the plant. Another indicator (indicator 2) for the condition of the plant is the plant vigor. The plant vigor becomes manifest in several aspects, too, some of which are visual appearance, e.g. leaf color, fruit color and aspect, amount of dead basal leaves and/or extent of leaf blades, plant weight, plant height, extent of plant verse (lodging), number, strong ness and productivity of tillers, panicles' length, extent of root system, strength of roots, extent of nodulation, in particular of rhizobial nodulation, point of time of germination, emergence, flowering, grain maturity and/or senescence, protein content, sugar content and the like. Another indicator (indicator 3) for an increase of a plant's health is the reduction of biotic or abiotic stress factors.

The three above mentioned indicators for the health condition of a plant may be interdependent and may result from each other. For example, a reduction of biotic or abiotic stress may lead to a better plant vigor, e.g. to better and bigger crops, and thus to an increased yield. Biotic stress, especially over longer terms, can have harmful effects on plants. The term "biotic stress" as used in the context of the present invention refers in particular to stress caused by living organisms. As a result, the quantity and the quality of the stressed plants, their crops and fruits decrease. As far as quality is concerned, reproductive development is usually severely affected with consequences on the crops which are important for fruits or seeds. Growth may be slowed by the stresses; polysaccharide synthesis, both structural and storage, may be reduced or modified: these effects may lead to a decrease in biomass and to changes in the nutritional value of the product. Abiotic stress includes drought, cold, increased UV, increased heat, or other changes in the environment of the plant, that leads to sub-optimal growth conditions. The term "increased yield" of a plant as used herein means that the yield of a product of the respective plant is increased by a measurable amount over the yield of the same product of the plant produced under the same conditions, but without the application of the composition of the invention. According to the present invention, it is preferred that the yield be increased by at least 0.5%, more preferred at least 1%, even more preferred at least 2%, still more preferred at least 4%. An increased yield may, for example, be due to a reduction of nitrification and a corresponding improvement of uptake of nitrogen nutrients. The term "improved plant vigor" as used herein means that certain crop characteristics are increased or improved by a measurable or noticeable amount over the same factor of the plant produced under the same conditions, but without the application of the composition of the present invention. Improved plant vigor can be characterized, among others, by following improved properties of a plant:
(a) improved vitality of the plant,
(b) improved quality of the plant and/or of the plant products, e.g.
(b) enhanced protein content,
(c) improved visual appearance,
(d) delay of senescence,
(e) enhanced root growth and/or more developed root system (e.g. determined by the dry mass of the root),
(f) enhanced nodulation, in particular rhizobial nodulation,
(g) longer panicles,
(h) bigger leaf blade,
(i) less dead basal leaves,
(j) increased chlorophyll content
(k) prolonged photosynthetically active period
(l) improved nitrogen-supply within the plant The improvement of the plant vigor according to the present invention particularly means that the improvement of anyone or several or all of the above mentioned plant characteristics are improved. It further means that if not all of the above characteristics are improved, those which are not improved are not worsened as compared to plants which were not treated according to the invention or are at least not worsened to such an extent that the negative effect exceeds the positive effect of the improved characteristic (i.e. there is always an overall positive effect which preferably results in an improved crop yield). An improved plant vigor may, for example, be due to a reduction of nitrification and, e.g. a regulation of plant growth.

In further embodiments, the composition may, in addition to the above indicated ingredients, in particular in addition to the nitrification inhibitor of the compound of formula I, further comprise one or more pesticides.

A pesticide is generally a chemical or biological agent (such as pesticidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:
(1) Microbial pesticides consist of bacteria, fungi or viruses (and often include the metabolites that bacteria and fungi produce). Entomopathogenic nematodes are also classed as microbial pesticides, even though they are multi-cellular.
(2) Biochemical pesticides are naturally occurring substances that control pests or provide other crop protection uses as defined below, but are relatively non-toxic to mammals.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

When living microorganisms, such as microbial pesticides from groups L1), L3) and L5), form part of such kit, it must be taken care that choice and amounts of the components (e. g. chemical pesticides) and of the further auxiliaries should not influence the viability of the microbial pesticides in the composition mixed by the user. Especially for bactericides and solvents, compatibility with the respective microbial pesticide has to be taken into account.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

The following list of pesticides I (e. g. pesticidally-active substances and biopesticides), in conjunction with which the compounds I can be used, is intended to illustrate the possible combinations but does not limit them:

A) Respiration inhibitors

Inhibitors of complex III at $Q_o$ site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[2-[[1-(4-chloro-phenyl)pyrazol-3-yl]oxymethyl]-3-methyl-phenyl]-4-methyl-tetrazol-5-one (A.1.25), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxy-methylen)phenyl)-3-methoxy-acrylic acid methylester (A.1.38);

inhibitors of complex III at $Q_i$ site: cyazofamid (A.2.1), amisulbrom (A.2.2), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A.2.3), fenpicoxamid (A.2.4);

inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), inpyrfluxam (A.3.22), pyrapropoyne (A.3.23), fluindapyr (A.3.28), methyl (E)-2-[2-[[(5-cyano-2-methylphenoxy)methyl]phenyl]-3-methoxy-prop-2-enoate (A.3.30), isoflucypram (A.3.31), 2-(difluoromethyl)-N-[(3R)-1,1,3-trimethyl-indan-4-yl)pyridine-3-carboxamide (A.3.32), 2-(difluoromethyl)-N-[(3R)-1,1,3-trimethylindan-4-yl]pyridine-3-carboxamide (A.3.33), 2-(difluoromethyl)-N-(3-ethyl-1,1-dimethyl-indan-4-yl)pyridine-3-carboxamide (A.3.34), 2-(difluoromethyl)-N-(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan-4-yl]pyridine-3-carboxamide (A.3.39);

other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e. g. fentin-acetate (A.4.8), fentin chloride (A.4.9) or fentin hydroxide (A.4.10); ametoctradin (A.4.11); silthiofam (A.4.12);

B) Sterol Biosynthesis Inhibitors (SBI fungicides)

C14 demethylase inhibitors: triazoles: azaconazole (B.1.1), bitertanol (B.1.2), bromu-conazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 2-(2,4-difluorophenyl)-1,1-difluoro-3-(tetrazol-1-yl)-1-[5-[4-(2,2,2-trifluoroethoxy)phenyl]-2-pyridyl]propan-2-ol (B.1.31), 2-(2,4-difluorophenyl)-1,1-difluoro-3-(tetrazol-1-yl)-1-[5-[4-(trifluoromethoxy)phenyl]-2-pyridyl]propan-2-ol (B.1.32), ipfentrifluconazole (B.1.37), mefentrifluconazole (B.1.38), 2-(chloromethyl)-2-methyl-5-(p-tolylmethyl)-1-(1,2,4-triazol-1-ylmethyl) cyclopentanol (B.1.43); imidazoles: imazalil (B.1.44), pefurazoate (B.1.45), prochloraz (B.1.46), triflumizol (B.1.47); pyrimidines, pyridines, piperazines: fenarimol (B.1.49), pyrifenox (B.1.50), triforine (B.1.51), [3-(4-chloro-2-fluoro-phenyl)-5-(2,4-difluorophenyl) isoxazol-4-yl]-(3-pyridyl)methanol (B.1.52);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

Other Sterol biosynthesis inhibitors: chlorphenomizole (B.4.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8);

D) Inhibitors of Cell Division and Cytoskeleton tubulin inhibitors: benomyl (D.1.1), carbendazim (D.1.2), fuberidazole (D1.3), thiabendazole (D.1.4), thiophanate-methyl (D.1.5), 3-chloro-4-(2,6-difluorophenyl)-6-methyl-5-phenyl-pyridazine (D.1.6), 3-chloro-6-methyl-5-phenyl-4-(2,4,6-trifluorophenyl)pyridazine (D.1.7), N-ethyl-2-[(3-ethynyl-8-methyl-6-quinolyl) oxy]butanamide (D.1.8), N-ethyl-2-[(3-ethynyl-8-methyl-6-quinolyl)oxy]-2-methylsulfanyl-acetamide (D.1.9), 2-[(3-ethynyl-8-methyl-6-quinol-yl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl-6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3-amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7); E) Inhibitors of amino acid and protein synthesis methionine synthesis inhibitors: cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6); F) Signal transduction inhibitors MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1); G) Lipid and membrane synthesis inhibitors Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acides: propamocarb (G.4.1);

inhibitors of oxysterol binding protein: oxathiapiprolin (G.5.1), 2-{3-[2-(1-{[3,5-bis(difluoro-methyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4-[1-[2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl]acetyl]-4-piperidyl]-N-tetralin-1-yl-pyridine-2-carboxamide (G.5.11);

H) Inhibitors With Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6M-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexa-dione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4-cyclopropyl-N-(2,4-dimethoxyphenyl)thiadiazole-5-carboxamide (J.1.10);

K) Unknown Mode of Action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), methasulfocarb (K.1.18), nitrapyrin (K.1.19), nitrothal-isopropyl (K.1.20), tolprocarb (K.1.21), oxincopper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N-methyl formamidine (K.1.27), N'-(4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenylz)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N'-[5-bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2-methyl-4-(3-trimethylsilanyl-propoxy)-phenyl)-N-ethyl-N-methyl formamidine (K.1.35), 2-(4-chlorophenyl)-N-[4-(3,4-dimethoxy-phenyl)-isoxazol-5-yl]-2-prop-2-ynyloxy-acetamide (K.1.36), 3-[5-(4-chlorophenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1-(4,6-dimethoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), 2-[2-[(7,8-difluoro-2- methyl-3-quinolyl)oxy]-6-fluoro-phenyl]propan-2-ol (K.1.44), 2-[2-fluoro-6-[(8-fluoro-2-methyl-3-quinolyl)oxy]phen-yl]propan-2-ol (K.1.45), quinofumelin (K.1.47), 9-fluoro-2,2-dimethyl-5-(3-quinolyl)-3H-1,4-benzoxazepine (K.1.49), 2-(6-benzyl-2-pyridyl)quinazoline (K.1.50), 2-[6-(3-fluoro-4-methoxy-phenyl)-5-methyl-2-pyridyl]quinazoline (K.1.51), dichlobentiazox (K.1.52), N'-(2,5-dimethyl-4-phenoxy-phenyl)-N-ethyl-N-methyl-formamidine (K.1.53), pyrifenamine (K.1.54).

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. moja vensis, B. mycoides, B. pumilus, B. simplex, B. solisalsi; B. subtilis, B. subtilis* var. *amyloliquefaciens, Candida oleophlla, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus alvei, Paenibacillus epiphyticus, P. polymyxa, Pantoea vagans, Penicillium bllaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia,* zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrIeGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecaniclllium longisporum, L. muscarium, Metarhizium anisopliae, M. anisopliae* var. *anisopliae, M. anisopliae* var. *acridum, Nomuraea rlleyi, Paecilomyces fumosoroseus, P. lilacinus, Paenibacillus poplliae, Pasteuria* spp., *P. nishizawae, P. penetrans, P. ramosa, P. thornea, P. usgae, Pseudomonas fluorescens, Spodoptera littoraks* nucleopolyhedrovirus (SpliNPV), *Steinemema carpocapsae, S. feltiae, S. kraussei, Streptomyces galbus, S. microflavus.*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,ZE)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, (R)-1-octen-3-ol, pentatermanone, (E,Z,Z)-3,8,11-tetradecatrienyl acetate, (Z,E)-9,12-tetradecadien-1-yl acetate, (Z)-7-tetradecen-2-one, (Z)-9-tetradecen-1-yl acetate, (Z)-11-tetradecenal, (Z)-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospialum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli, R. I.* bv. *trifolii, R. I.* bv. *viciae, R. tropici, Sinorhizobium meliloti.*

M) Insecticides

M.1) Acetylcholine esterase (AChE) inhibitors: M.1A carbamates, e.g. aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or M.1B organophosphates, e.g. acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, and vamidothion;

M.2) GABA-gated chloride channel antagonists: M.2A cyclodiene organochlorine compounds, e.g. endosulfan or chlordane; or M.2B fiproles (phenylpyrazoles), e.g. ethiprole, fipronil, flufiprole, pyrafluprole, and pyriprole;

M.3) Sodium channel modulators from the class of M.3A pyrethroids, e.g. acrinathrin, allethrin, d-cis-trans allethrin, d-trans allethrin, bifenthrin, kappa-bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, epsilon-momfluorothrin, permethrin, phenothrin, prallethrin, profluthrin, pyrethrin (pyrethrum), resmethrin, silafluofen, tefluthrin, kappa-tefluthrin, tetramethylfluthrin, tetramethrin, tralomethrin, and transfluthrin; or M.3B sodium channel modulators such as DDT or methoxychlor;

M.4) Nicotinic acetylcholine receptor agonists (nAChR): M.4A neonicotinoids, e.g. acetamiprid, clothianidin, cycloxaprid, dinotefuran, imidacloprid, nitenpyram, thiacloprid and thiamethoxam; or the compounds M.4A.1 4,5-Dihydro-N-nitro-1-(2-oxiranylmethyl)-

1H-imidazol-2-amine, M.4A.2: (2E–)-1-[(6-Chloro-pyridin-3-yl)methyl]-N'-nitro-2-pentylidenehydrazin-ecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or M.4B nicotine; M.4C sulfoxaflor; M.4D flupyradifurone; M.4E triflumezopyrim;

M.5) Nicotinic acetylcholine receptor allosteric activators:spinosyns, e.g. spinosad or spinetoram;

M.6) Chloride channel activators from the class of avermectins and milbemycins, e.g. abamectin, emamectin benzoate, ivermectin, lepimectin, or milbemectin;

M.7) Juvenile hormone mimics, such as M.7A juvenile hormone analogues hydroprene, kinoprene, and methoprene; or M.7B fenoxycarb, or M.7C pyriproxyfen;

M.8) miscellaneous non-specific (multi-site) inhibitors, e.g. M.8A alkyl halides as methyl bromide and other alkyl halides, M.8B chloropicrin, M.8C sulfuryl fluoride, M.8D borax, or M.8E tartar emetic;

M.9) Chordotonal organ TRPV channel modulators, e.g. M.9B pymetrozine; pyrifluquinazon; M.10 Mite growth inhibitors, e.g. M.10A clofentezine, hexythiazox, and diflovidazin, or M.10B etoxazole;

M.10) Mite growth inhibitors, e.g. M.10A clofentezine, hexythiazox, and diflovidazin, or M.10B etoxazole;

M.11) Microbial disruptors of insect midgut membranes, e.g. *Bacillus thuringiensis* or *Bacillus sphaericus* and the insecticdal proteins they produce such as *Bacillus thuringiensis* subsp. *israelensis*, *Bacillus sphaericus*, *Bacillus thuringiensis* subsp. *aizawai*, *Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb, and Cry34/35Ab1;

M.12) Inhibitors of mitochondrial ATP synthase, e.g. M.12A diafenthiuron, or M.12B organotin miticides such as azocyclotin, cyhexatin, or fenbutatin oxide, M.12C propargite, or M.12D tetradifon;

M.13) Uncouplers of oxidative phosphorylation via disruption of the proton gradient, e.g. chlorfenapyr, DNOC, or sulfluramid;

M.14) Nicotinic acetylcholine receptor (nAChR) channel blockers, e.g. nereistoxin analogues bensultap, cartap hydrochloride, thiocyclam, or thiosultap sodium;

M.15) Inhibitors of the chitin biosynthesis type 0, such as benzoylureas e.g. bistrifluron, chlorfluazuron, diflubenzuron, flucycloxuron, flufenoxuron, hexaflumuron, lufenuron, novaluron, noviflumuron, teflubenzuron, or triflumuron;

M.16) Inhibitors of the chitin biosynthesis type 1, e.g. buprofezin;

M.17) Moulting disruptors, Dipteran, e.g. cyromazine;

M.18) Ecdyson receptor agonists such as diacylhydrazines, e.g. methoxyfenozide, tebufenozide, halofenozide, fufenozide, or chromafenozide;

M.19) Octopamin receptor agonists, e.g. amitraz;

M.20) Mitochondrial complex III electron transport inhibitors, e.g. M.20A hydramethylnon, M.20B acequinocyl, M.20C fluacrypyrim; or M.20D bifenazate;

M.21) Mitochondrial complex I electron transport inhibitors, e.g. M.21A METI acaricides and insecticides such as fenazaquin, fenpyroximate, pyrimidifen, pyridaben, tebufenpyrad or tolfenpyrad, or M.21B rotenone;

M.22) Voltage-dependent sodium channel blockers, e.g. M.22A indoxacarb, M.22B metaflumizone, e.g. M.22B.1: 2-[2-(4-Cyanophenyl)-1-[3-(trifluoromethyl) phenyl]-ethylidene]-N-[4-(difluoromethoxy)phenyl]-hydrazinecarboxamide or M.22B.2: N-(3-Chloro-2-methylphenyl)-2-[(4-chlorophenyl)[4-[methyl (methylsulfonyl)amino]phenyl]-methylene]-hydrazinecarboxamide;

M.23) Inhibitors of the of acetyl CoA carboxylase, such as Tetronic and Tetramic acid derivatives, e.g. spirodiclofen, spiromesifen, or spirotetramat; M.23.1 spiropidion;

M.24) Mitochondrial complex IV electron transport inhibitors, e.g. M.24A phosphine such as aluminium phosphide, calcium phosphide, phosphine or zinc phosphide, or M.24B cyanide;

M.25) Mitochondrial complex II electron transport inhibitors, such as beta-ketonitrile derivatives, e.g. cyenopyrafen or cyflumetofen;

M.28) Ryanodine receptor-modulators from the class of diamides, e.g. flubendiamide, chlor-antraniliprole, cyantraniliprole, tetraniliprole, M.28.1: (R)-3-Chlor-N1-{2-methyl-4-[1,2,2,2-tetrafluoro-1-(trifluoromethyl) ethyl]phenyl}-N2-(1-methyl-2-methylsulfonylethyl) phthalamid, M.28.2: (S)-3-Chloro-N1-{2-methyl-4-[1, 2,2,2-tetrafluoro-1-(trifluoromethyl)ethyl]phenyl}-N2-(1-methyl-2-methylsulfonylethyl)phthalamid, M.28.3: cyclaniliprole, or M.28.4: methyl-2-[3,5-dibromo-2-({ [3-bromo-1-(3-chlorpyrid in-2-yl)-1H-pyrazol-5-yl] carbonyl}amino)benzoyl]-1,2-dimethylhydrazinecarboxylate; or M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl) pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene) carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) 3-Bromo-N-[2,4-d ichloro-6-(methylcarbamoyl)phenyl]-1-(3,5-d ichloro-2-pyridyl)-1H-pyrazole-5-carboxamide; M.28.5l) N-[4-Chloro-2-[[(1,1-dimethylethyl)amino]carbonyl]-6-methyl-phenyl]-1-(3-chloro-2-pyridinyl)-3-(fluoromethoxy)-1H-pyrazole-5-carboxamide; or M.28.6: cyhalodiamide; or M.29) Chordotonal organ Modulators—undefined target site, e.g. flonicamid;

M.UN. insecticidal active compounds of unknown or uncertain mode of action, e.g. afido-pyropen, afoxolaner, azadirachtin, amidoflumet, benzoximate, broflanilide, bromopropylate, chinomethionat, cryolite, dicloromezotiaz, dicofol, flufenerim, flometoquin, fluensulfone, fluhexafon, fluopyram, fluralaner, metaldehyde, metoxadiazone, piperonyl butoxide, pyflubumide, pyridalyl, tioxazafen, M.UN.3: 11-(4-chloro-2,6-dimethylphenyl)-12-hydroxy-1,4-dioxa-9-azadispiro [4.2.4.2]-tetradec-11-en-10-one, M.UN.4: 3-(4'-fluoro-2,4-dimethylbiphenyl-3-yl)-4-hydroxy-8-oxa-1-azaspiro[4.5]dec-3-en-2-one, M. U N.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, 1-1582);

M.UN.6: flupyrimin;

M.UN.8: fluazaindolizine; M.UN.9.a): 4-[5-(3,5-dichlorophenyl)-5-(trifluoromethyl)-4H-isoxazol-3-yl]-2-methyl-N-(1-oxothietan-3-yl)benzamide; M.UN.9.b): fluxametamide;

M.UN.10: 5[3-[2,6-dichloro-4-(3,3-dichloroallyloxy)phenoxy]propoxy]-1H-pyrazole;

M.UN.11.i) 4-cyano-N-[2-cyano-5-[[2,6-dibromo-4[1,2,2,3,3,3-hexafluoro-1-(trifluoromethyl)propyl]phenyl]carbamoyl]phenyl]-2-methyl-benzamide; M.UN.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.UN.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M.UN.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.UN.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.UN.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.UN.11.o) 4-cyano-N-[2-cyano-5-[[2,6-dichloro-4-[1,2,2,2-tetrafluoro-1-(trifluoromethypethyl]phenyl]carbamoyl]phenyl]-2-methyl-benzamide; M.UN.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or M.UN.12.a) 2-(1,3-Dioxan-2-yl)-6[2-(3-pyridinyl)-5-thiazolyl]-pyridine; M.UN.12.b) 2-[6-[2-(5-Fluoro-3-pyridinyl)-5-thiazolyl]-2-pyridinyl]-pyrimidine; M.UN.12.c) 2-[6-[2-(3-Pyridinyl)-5-thiazolyl]-2-pyridinyl]-pyrimidine; M.UN.12.d) N-Methylsulfonyl-6-[2-(3-pyridyl)thiazol-5-yl]pyridine-2-carboxamide; M.UN.12.e) N-Methylsulfonyl-6-[2-(3-pyridyl)thiazol-5-yl]pyridine-2-carboxamide;

M.UN.14a) 1-[(6-Chloro-3-pyridinyl)methyl]-1,2,3,5,6,7-hexahydro-5-methoxy-7-methyl-8-nitro-imidazo[1,2-a]pyridine; or M.UN.14b) 1-[(6-Chloropyridin-3-yl)methyl]-7-methyl-8-nitro-1,2,3,5,6,7-hexahydroimidazo[1,2-a]pyridin-5-ol;

M.UN.16a) 1-isopropyl-N,5-dimethyl-N-pyridazin-4-yl-pyrazole-4-carboxamide; or M.UN.16b) 1-(1,2-dimethylpropyl)-N-ethyl-5-methyl-N-pyridazin-4-yl-pyrazole-4-carboxamide; M.UN.16c) N,5-dimethyl-N-pyridazin-4-yl-1-(2,2,2-trifluoro-1-methyl-ethyl)pyrazole-4-carboxamide; M.UN.16d) 1-[1-(1-cyanocyclopropypethyl]-N-ethyl-5-methyl-N-pyridazin-4-yl-pyrazole-4-carboxamide; M.UN.16e) N-ethyl-1-(2-fluoro-1-methyl-propyl)-5-methyl-N-pyridazin-4-yl-pyrazole-4-carboxamide; M.UN.16f) 1-(1,2-dimethylpropyl)-N,5-dimethyl-N-pyridazin-4-yl-pyrazole-4-carboxamide; M.UN.16g) 1-[1-(1-cyanocyclopropyl)ethyl]-N,5-dimethyl-N-pyridazin-4-yl-pyrazole-4-carboxamide; M.UN.16h) N-methyl-1-(2-fluoro-1-methyl-propyl)-5-methyl-N-pyridazin-4-yl-pyrazole-4-carboxamide; M.UN.16i) 1-(4,4-difluorocyclohexyl)-N-ethyl-5-methyl-N-pyridazin-4-yl-pyrazole-4-carboxamide; or M.UN.16j) 1-(4,4-difluorocyclohexyl)-N,5-dimethyl-N-pyridazin-4-yl-pyrazole-4-carboxamide, M.UN.17a) N-(1-methylethyl)-2-(3-pyridinyl)-2H-indazole-4-carboxamide; M.UN.17b) N-cyclopropyl-2-(3-pyridinyl)-2H-indazole-4-carboxamide; M.UN.17c) N-cyclohexyl-2-(3-pyridinyl)-2H-indazole-4-carboxamide; M.UN.17d) 2-(3-pyridinyl)-N-(2,2,2-trifluoroethyl)-2H-indazole-4-carboxamide; M.UN.17e) 2-(3-pyridinyl)-N-[(tetrahydro-2-furanyl)methyl]-2H-indazole-5-carboxamide; M.UN.17f) methyl 2-[[2-(3-pyridinyl)-2H-indazol-5-yl]carbonyl]hydrazinecarboxylate; M.UN.17g) N-[(2,2-difluorocyclopropyl)methyl]-2-(3-pyridinyl)-2H-indazole-5-carboxamide; M.UN.17h) N-(2,2-difluoropropyl)-2-(3-pyridinyl)-2H-indazole-5-carboxamide; M.UN.17i) 2-(3-pyridinyl)-N-(2-pyrimidinylmethyl)-2H-indazole-5-carboxamide; M.UN.17j) N-[(5-methyl-2-pyrazinyl)methyl]-2-(3-pyridinyl)-2H-indazole-5-carboxamide, M.UN.18. tyclopyrazoflor;

M.UN.19 sarolaner, M.UN.20 lotilaner;

M.UN.21 N-[4-Chloro-3-[[phenylmethyl)amino]carbonyl]phenyl]-1-methyl-3-(1,1,2,2,2-pentafluoroethyl)-4-(trifluoromethyl)-1H-pyrazole-5-carboxamide; M.UN.22a 2-(3-ethylsulfonyl-2-pyridyl)-3-methyl-6-(trifluoromethyl)imidazo[4,5-b]pyridine, or M.UN.22b 2-[3-ethylsulfonyl-5-(trifluoromethyl)-2-pyridyl]-3-methyl-6-(trifluoromethypimidazo[4,5-b]pyridine;

M.UN.23a) 4-[5-(3,5-dichlorophenyl)-5-(trifluoromethyl)-4H-isoxazol-3-yl]-N-[(4R)-2-ethyl-3-oxo-isoxazolidin-4-yl]-2-methyl-benzamide, or M.UN.23b) 4-[5-(3,5-dichloro-4-fluoro-phenyl)-5-(trifluoromethyl)-4H-isoxazol-3-yl]-N-[(4R)-2-ethyl-3-oxo-isoxazolidin-4-yl]-2-methyl-benzamide;

M.UN.24a) N-4-[4-chloro-3-(cyclopropylcarbamoyl)phenyl]-2-methyl-5-(1,1,2,2,2-pentafluoroethyl)-4-(trifluoromethyl)pyrazole-3-carboxamide or M.UN.24b) N-[4-chloro-3-[(1-cyanocyclopropyl)carbamoyl]phenyl]-2-methyl-5-(1,1,2,2,2-pentafluoroethyl)-4-(trifluoromethyl)pyrazole-3-carboxamide; M.UN.25 acynonapyr; M.UN.26 benzpyrimoxan; M.UN.27 2-chloro-N-(1-cyanocyclopropyl)-5-[1-[2-methyl-5-(1,1,2,2,2-pentafluoroethyl)-4-(trifluoromethyppyrazol-3-yl]pyrazol-4-yl]benzamide; M.UN.28 Oxazosulfyl;

M.UN.29a) [(2S,3R,4R,5S,6S)-3,5-dimethoxy-6-methyl-4-propoxy-tetrahydropyran-2-yl] N-[4-[1-[4-(trifluoromethoxy)phenyl]-1,2,4-triazol-3-yl]phenyl]carbamate; M.UN.29b) [(2S,3R,4R,5S,6S)-3,4,5-trimethoxy-6-methyl-tetrahydropyran-2-yl] N-[4-[1-[4-(trifluoromethoxy)phenyl]-1,2,4-triazol-3-yl]phenyl]carbamate; M.UN.29c) [(2S,3R,4R,5S,6S)-3,5-dimethoxy-6-methyl-4-propoxy-tetrahydropyran-2-yl] N-[4-[1-[4-(1,1,2,2,2-pentafluoroethoxy)phenyl]-1,2,4-triazol-3-yl]phenyl]carbamate; M.UN.29d) [(2S,3R,4R,5S,6S)-3,4,5-trimethoxy-6-methyl-tetrahydropyran-2-yl] N-[4-[1-[4-(1,1,2,2,2-pentafluoroethoxy)phenyl]-1,2,4-triazol-3-yl]phenyl]carbamate; M.UN.29.e) (2Z)-3-(2-isopropylphenyl)-2-[(E)-[4-[1-[4-(trifluoromethoxy)phenyl]-1,2,4-triazol-3-yl]phenyl]methylenehydrazono]thiazolidin-4-one or M.UN.29f) (2Z)-3-(2-isopropylphenyl)-2-[(E)-[4-[1-[4-(1,1,2,2,2-pentafluoroethoxy)phenyl]-1,2,4-triazol-3-yl]phenyl]methylenehydrazono]thiazolidin-4-one.

N) Herbicides herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, or ureas.

The present invention furthermore relates to agrochemical compositions comprising a mixture of at least one compound of formula I, i.e. a nitrification inhibitor of the present invention (compound I or component I) and at least one further active substance useful for plant protection, e. g. selected from the groups A) to N) (component 2), in particular one further herbicide selected from the group N).

By applying compounds I together with at least one active substance from groups A) to N) a synergistic plant health effect can be obtained, i.e. more than simple addition of the individual effects is obtained (synergistic mixtures).

This can be obtained by applying the compounds I and at least one further active substance simultaneously, either jointly (e. g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide I sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In case of a mixture comprising a pesticide II selected from group L), it is preferred that the pesticide I is applied as last treatment.

According to the invention, the solid material (dry matter) of the biopesticides (with the exception of oils such as Neem oil, Tagetes oil, etc.) are considered as active components (e. g. to be obtained after drying or evaporation of the extraction medium or the suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the binary mixtures and compositions, the weight ratio of the component 1) and the component 2) usually is in the range of from 1000:1 to 1:1, often in the range of from 100: 1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to further embodiments of the mixtures and compositions, the weight ratio of the component 1) and the component 2) generally depends from the properties of the active components used, usually it is in the range of from 1:10,000 to 10,000:1, regularly in the range of from 1:100 to 10,000:1, preferably in the range of from 1:100 to 5,000:1, more preferably in the range of from 1:1 to 1,000:1, even more preferably in the range of from 1:1 to 500:1 and in particular in the range of from 10:1 to 300:1.

According to further embodiments of the mixtures and compositions, the weight ratio of the component 1) and the component 2) usually is in the range of from 20,000:1 to 1:10, often in the range of from 10,000:1 to 1:1, regularly in the range of from 5,000:1 to 5:1, preferably in the range of from 5,000:1 to 10:1, more preferably in the range of from 2,000:1 to 30:1, even more preferably in the range of from 2,000:1 to 100:1 and in particular in the range of from 1,000:1 to 100:1.

According to further embodiments of the mixtures and compositions, the weight ratio of the component 1) and the component 2) usually is in the range of from 1:20,000 to 10:1, often in the range of from 1:10,000 to 1:1, regularly in the range of from 1:5,000 to 1:5, preferably in the range of from 1:5,000 to 1:10, more preferably in the range of from 1:2,000 to 1:30, even more preferably in the range of from 1:2,000 to 1:100 and in particular in the range of from 1:1,000 to 1:100.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

The active substances listed under groups A) to K), their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441). Some compounds are identified by their CAS Registry Number which is separated by hyphens into three parts, the first consisting from two up to seven digits, the second consisting of two digits, and the third consisting of a single digit.

The commercially available compounds of the group M listed above may be found in The Pesticide Manual, 17th Edition, C. MacBean, British Crop Protection Council (2015) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 cycloxaprid is known from WO 2010/069266 and WO 2011/069456. M.4A.1 is known from CN 103814937; CN105367557, CN 105481839. M.4A.2, guadipyr, is known from WO 2013/003977, and M.4A.3 (approved as paichongding in China) is known from WO 2007/101369. M.22B.1 is described in CN10171577 and M.22B.2 in CN102126994. Spiropidion M.23.1 is known from WO 2014/191271. M.28.1 and M.28.2 are known from WO 2007/101540. M.28.3 is described in WO 2005/077934. M.28.4 is described in WO 2007/043677. M.28.5a) to M.28.5d) and M.28.5h) are described in WO 2007/006670, WO 2013/024009 and WO 2013/024010, M.28.5i) is described in WO 2011/085575, M.28.5j) in WO 2008/134969, M.28.5k) in US2011/046186 and M.28.5l) in WO 2012/034403. M.28.6 can be found in WO 2012/034472. M.UN.3 is known from WO 2006/089633 and M.UN.4 from WO 2008/067911. M.UN.5 is described in WO 2006/043635, and biological control agents on the basis of *Bacil-*

*lus firmus* are described in WO 2009/124707. Flupyrimin is described in WO 2012/029672. M.UN.8 is known from WO 2013/055584. M.UN.9.a) is described in WO 2013/050317. M.UN.9.b) is described in WO 2014/126208. M.UN.10 is known from WO 2010/060379. Broflanilide and M.UN.11.b) to M.UN.11.h) are described in WO 2010/018714, and M.UN.11i) to M.UN.11.p) in WO 2010/127926. M.UN.12.a) to M.UN.12.c) are known from WO 2010/006713, M.UN.12.d) and M.UN.12.e) are known from WO 2012/000896. M.UN.14a) and M.UN.14b) are known from WO 2007/101369. M.UN.16.a) to M.UN.16h) are described in WO 2010/034737, WO 2012/084670, and WO 2012/143317, resp., and M.UN.16i) and M.UN.16j) are described in WO 2015/055497. M.UN.17a) to M.UN.17.j) are described in WO 2015/038503. M.UN.18 Tycloprazoflor is described in US2014/0213448. M.UN.19 is described in WO 2014/036056. M.UN.20 is known from WO 2014/090918. M.UN.21 is known from EP2910126. M.UN.22a and M.UN.22b are known from WO 2015/059039 and WO 2015/190316. M.UN.23a and M.UN.23b are known from WO 2013/050302. M.UN.24a) and M.UN.24b) are known from WO 2012/126766. Acynonapyr M.UN.25 is known from WO 2011/105506. Benzpyrimoxan M.UN.26 is known from WO 2016/104516. M.UN.27 is known from WO 2016/174049. M.UN.28 Oxazosulfyl is known from WO 2017/104592. M.UN.29a) to M.UN.29f) are known from WO 2009/102736 or WO 2013116053.

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity. Many of these biopesticides have been deposited under deposition numbers mentioned herein (the prefices such as ATCC or DSM refer to the acronym of the respective culture collection, for details see e. g. here: http://www.wfcc.info/ccinfo/collection/by_acronym/), are referred to in literature, registered and/or are commercially available: mixtures of *Aureobasidium pullulans* DSM 14940 and DSM 14941 isolated in 1989 in Konstanz, Germany (e. g. blastospores in Blossom Protect® from bio-ferm GmbH, Austria), Azospirillum brasilense Sp245 originally isolated in wheat reagion of South Brazil (Passo Fundo) at least prior to 1980 (BR 11005; e. g. GELFIX® Gramíneas from BASF Agricultural Specialties Ltd., Brazil), *A. brasilense* strains Ab-V5 and Ab-V6 (e. g. in AzoMax from Novozymes BioAg Produtos papra Agricultura Ltda., Quattro Barras, Brazil or Simbiose-Maiz® from Simbiose-Agro, Brazil; Plant Soil 331, 413-425, 2010), *Bacillus amyloliquefaciens* strain AP-188 (NRRL B-50615 and B-50331; U.S. Pat. No. 8,445, 255); *B. amyloliquefaciens* spp. *plantarum* D747 isolated from air in Kikugawa-shi, Japan (US 20130236522 A1; FERM BP-8234; e. g. Double Nickel™ 55 WDG from Certis LLC, USA), *B. amyloliquefaciens* spp. *plantarum* FZB24 isolated from soil in Brandenburg, Germany (also called SB3615; DSM 96-2; J. Plant Dis. Prot. 105, 181-197, 1998; e. g. Taegro® from Novozyme Biologicals, Inc., USA), *B. amyloliquefaciens* ssp. *plantarum* FZB42 isolated from soil in Brandenburg, Germany (DSM 23117; J. Plant Dis. Prot. 105, 181-197, 1998; e. g. RhizoVital® 42 from AbiTEP GmbH, Germany), *B. amyloliquefaciens* ssp.

*plantarum* MBI600 isolated from faba bean in Sutton Bonington, Nottinghamshire, U.K. at least before 1988 (also called 1430; NRRL B-50595; US 2012/0149571 A1; e. g. Integral® from BASF Corp., USA), *B. amyloliquefaciens* spp. *plantarum* QST-713 isolated from peach orchard in 1995 in California, U.S.A. (NRRL B-21661; e. g. Serenade® MAX from Bayer Crop Science LP, USA), *B. amyloliquefaciens* spp. *plantarum* TJ1000 isolated in 1992 in South Dakoda, U.S.A. (also called 1BE; ATCC BAA-390; CA 2471555 A1; e. g. QuickRoots™ from TJ Technologies, Watertown, SD, USA), *B. firmus* CNCM 1-1582, a variant of parental strain EIP-N1 (CNCM 1-1556) isolated from soil of central plain area of Israel (WO 2009/126473, U.S. Pat. No. 6,406,690; e. g. Votivo® from Bayer CropScience LP, USA), *B. pumllus* GHA 180 isolated from apple tree rhizosphere in Mexico (IDAC 260707-01; e. g. PRO-MIX® BX from Premier Horticulture, Quebec, Canada), *B. pumllus* INR-7 otherwise referred to as BU-F22 and BU-F33 isolated at least before 1993 from cucumber infested by *Erwinia tracheiphlla* (NRRL B-50185, NRRL B-50153; U.S. Pat. No. 8,445,255), *B. pumilus* KFP9F isolated from the rhizosphere of grasses in South Africa at least before 2008 (NRRL B-50754; WO 2014/029697; e. g. BAC-UP or FUSION-P from BASF Agricultural Specialities (Pty) Ltd., South Africa), *B. pumllus* QST 2808 was isolated from soil collected in Pohnpei, Federated States of Micronesia, in 1998 (NRRL B-30087; e. g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* ssp. *aizawai* ABTS-1857 isolated from soil taken from a lawn in Ephraim, Wisconsin, U.S.A., in 1987 (also called ABG-6346; ATCC SD-1372; e. g. XenTari® from BioFa AG, Munsingen, Germany), *B. t.* ssp. *kurstaki* ABTS-351 identical to HD-1 isolated in 1967 from diseased Pink Bollworm black larvae in Brownsville, Texas, U.S.A. (ATCC SD-1275; e. g. Dipel® DF from Valent BioSciences, IL, USA), *B. t.* ssp. *kurstaki* SB4 isolated from *E. saccharina* larval cadavers (NRRL B-50753; e. g. Beta Pro® from BASF Agricultural Specialities (Pty) Ltd., South Africa), *B. t.* ssp. *tenebrionis* NB-176-1, a mutant of strain NB-125, a wild type strain isolated in 1982 from a dead pupa of the beetle Tenebrio molitor (DSM 5480; EP 585 215 B1; e. g. Novodor® from Valent BioSciences, Switzerland), *Beauveria bassiana* GHA (ATCC 74250; e. g. BotaniGard® 22WGP from Laverlam Int. Corp., USA), *B. bassiana* JW-1 (ATCC 74040; e. g. Naturalis® from CBC (Europe) S.r.l., Italy), *B. bassiana* PPRI 5339 isolated from the larva of the tortoise beetle *Conchyloctenia punctata* (NRRL 50757; e. g. BroadBand® from BASF Agricultural Specialities (Pty) Ltd., South Africa), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e. g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e. g. GELFIX 5 or ADHERE 60 from BASF Agricultural Specialties Ltd., Brazil), *B. japonicum* SEMIA 5080 obtained under lab condtions by Embrapa-Cerrados in Brazil and used in commercial inoculants since 1992, being a natural variant of SEMIA 586 (CB1809) originally isolated in U.S.A. (CPAC 7; e. g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e. g. Contans® WG, Intercept® WG from Bayer CropScience AG, Germany), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e. g. Gemstar® from Certis LLC, USA), *Helicoverpa zea* nucleopolyhedrovirus ABA-NPV-U (e. g. Heligen® from AgBiTech Pty Ltd., Queensland, Australia), *Heterorhabditis bacteriophora* (e. g. Nemasys® G from BASF Agricultural Specialities Limited, UK), *Isaria fumosorosea* Apopka-97 isolated from mealy bug on gynura in Apopka, Florida, U.S.A. (ATCC 20874; Biocontrol Science Technol. 22(7), 747-761, 2012; e. g. PFR-97™ or PreFeRal® from Certis LLC, USA), *Metarhizium anisopliae* var. *anisopliae* F52 also called 275 or V275 isolated from codling moth in Austria (DSM 3884, ATCC 90448; e. g. Met52® Novozymes Biologicals BioAg Group, Canada), *Metschnikowia fructicola* 277 isolated from grapes in the central part of Israel (U.S. Pat. No. 6,994,849; NRRL Y-30752; e. g. formerly Shemer® from Agrogreen, Israel), *Paecilomyces ilacinus* 251 isolated from infected nematode eggs in the Philippines (AGAL 89/030550; WO 1991/02051; Crop Protection 27, 352-361, 2008; e. g. BioAct® from Bayer CropScience AG, Germany and MeloCon® from Certis, USA), *Paenibacillus alvei* NAS6G6 isolated from the rhizosphere of grasses in South Africa at least before 2008 (WO 2014/029697; NRRL B-50755; e.g. BAC-UP from BASF Agricultural Specialities (Pty) Ltd., South Africa), *Paenibacillus* strains isolated from soil samples from a variety of European locations including Germany: *P. epiphyticus* Lu17015 (WO 2016/020371; DSM 26971), *P. polymyxa* ssp. *plantarum* Lu16774 (WO 2016/020371; DSM 26969), *P. p.* ssp. *plantarum* strain Lu17007 (WO 2016/020371; DSM 26970); *Pasteuria nishizawae* Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilaii*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *Reynoutria sachalinensis* extract (EP 0307510 B1; e. g. Regalia® SC from Marrone Biolnnovations, Davis, CA, USA or Milsana® from BioFa AG, Germany), *Steinernema carpocapsae* (e. g. Millenium® from BASF Agricultural Specialities Limited, UK), *S. feltiae* (e. g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *Trichoderma asperelloides* JM41R isolated in South Africa (NRRL 50759; also referred to as *T. fertile*; e. g. Trichoplus® from BASF Agricultural Specialities (Pty) Ltd., South Africa), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, OH, USA).

According to one embodiment of the inventive mixtures, the at least one pesticide II is selected from the groups L1) to L6):

L1) Microbial pesticides with fungicidal, bactericidal, viricidal and/or plant defense activator activity: *Aureobasidium pullulans* DSM 14940 and DSM 14941 (L1.1), *Bacillus amyloliquefaciens* AP-188 (L.1.2), *B. amyloliquefaciens* ssp. *plantarum* D747 (L.1.3), *B. amyloliquefaciens* ssp. *plantarum* FZB24 (L.1.4), *B. amyloliquefaciens* ssp. *plantarum* FZB42 (L.1.5), *B. amyloliquefaciens* ssp. *plantarum* MBI600 (L.1.6), *B. amyloliquefaciens* ssp. *plantarum* QST-713 (L.1.7), *B. amyloliquefaciens* ssp. *plantarum* TJ1000 (L.1.8), *B. pumilus* GB34 (L.1.9), *B. pumilus* GHA 180 (L.1.10), *B. pumilus* INR-7 (L.1.11), *B. pumilus* QST 2808 (L.1.13), *B. simplex* ABU 288 (L.1.14), *B. subtilis* FB1 7 (L.1.15), *Coniothyrium minitans* CON/M/91-08 (L.1.16), *Metschnikowia fructicola* NRRL Y-30752 (L.1.17), *Penicillium bilaiae* ATCC 22348 (L.1.19), *P. bilaiae* ATCC 20851 (L.1.20), *Penicillium bilaiae* ATCC 18309 (L.1.21), *Streptomyces microflavus* NRRL B-50550 (L.1.22), *T. harzianum* T-22 (L.1.24);

L2) Biochemical pesticides with fungicidal, bactericidal, viricidal and/or plant defense activator activity: harpin protein (L.2.1), *Reynoutria sachalinensis* extract (L.2.2);

L3) Microbial pesticides with insecticidal, acaricidal, molluscidal and/or nematicidal activity: *Bacillus firmus* I-1582 (L.3.1); *B. thuringiensis* ssp. *aizawai* ABTS-1857 (L.3.2), *B. t.* ssp. *kurstaki* ABTS-351 (L.3.3), *B. t.* ssp. *tenebrionis* NB-176-1 (L.3.5), *Beauvena bassiana* GHA (L.3.6), *B. bassiana* JW-1 (L.3.7), *Burkholderia* sp. A396 (L.3.9), *Helicoverpa armigera* nucleopolyhedrovirus (HearNPV) (L.3.10), *Helicoverpa zea* nucleopolyhedrovirus (HzNPV) ABA-NPV-U (L.3.11), *Helicoverpa zea* single capsid nucleopolyhedrovirus (HzSNPV) (L.3.12), *Heterohabditis bacteriophora* (L.3.13), *Isaria fumosorosea* Apopka-97 (L.3.14), *Metarhizium anisopliae* var. *anisopliae* F52 (L.3.15), *Paecilomyces lilacinus* 251 (L.3.16), *Pasteuria nishizawae* Pn1 (L.3.17), *Steinernema carpocapsae* (L.3.18), *S. feltiae* (L.3.19);

L4) Biochemical pesticides with insecticidal, acaricidal, molluscidal, pheromone and/or nematicidal activity: cis-jasmone (L.4.1), methyl jasmonate (L.4.2), Quillay extract (L.4.3);

L5) Microbial pesticides with plant stress reducing, plant growth regulator, plant growth promoting and/or yield enhancing activity.

In a further aspect the present invention relates to an agrochemical mixture comprising at least one fertilizer; and at least one nitrification inhibitor as defined as defined herein above; or at least one fertilizer and a composition as mentioned above.

In the terms of the present invention "agrochemical mixture" means a combination of at least two compounds. The term is, however, not restricted to a physical mixture comprising at least two compounds, but refers to any preparation form of at least one compound and at least one further compound, the use of which many be time- and/or locus-related.

The agrochemical mixtures may, for example, be formulated separately but applied in a temporal relationship, i.e. simultaneously or subsequently, the subsequent application having a time interval which allows a combined action of the compounds.

Furthermore, the individual compounds of the agrochemical mixtures according to the invention such as parts of a kit or parts of the binary mixture may be mixed by the user himself in a suitable mixing device. In specific embodiments further auxiliaries may be added, if appropriate.

The term "fertilizers" is to be understood as chemical compounds applied to promote plant and fruit growth. Fertilizers are typically applied either through the soil (for uptake by plant roots), through soil substituents (also for uptake by plant roots), or by foliar feeding (for uptake through leaves). The term also includes mixtures of one or more different types of fertilizers as mentioned below.

The term "fertilizers" can be subdivided into several categories including: a) organic fertilizers (composed of decayed plant/animal matter), b) inorganic fertilizers (composed of chemicals and minerals) and c) urea-containing fertilizers.

Organic fertilizers include manure, e.g. liquid manure, semi-liquid manure, biogas manure, stable manure or straw manure, slurry, worm castings, peat, seaweed, compost, sewage, and guano. Green manure crops are also regularly grown to add nutrients (especially nitrogen) to the soil. Manufactured organic fertilizers include compost, blood meal, bone meal and seaweed extracts. Further examples are enzyme digested proteins, fish meal, and feather meal. The decomposing crop residue from prior years is another source of fertility. In addition, naturally occurring minerals such as mine rock phosphate, sulfate of potash and limestone are also considered inorganic fertilizers.

Inorganic fertilizers are usually manufactured through chemical processes (such as the Haber process), also using naturally occurring deposits, while chemically altering them (e.g. concentrated triple superphosphate). Naturally occurring inorganic fertilizers include Chilean sodium nitrate, mine rock phosphate, limestone, and raw potash fertilizers.

The inorganic fertilizer may, in a specific embodiment, be a NPK fertilizer. "NPK fertilizers" are inorganic fertilizers formulated in appropriate concentrations and combinations comprising the three main nutrients nitrogen (N), phosphorus (P) and potassium (K) as well as typically S, Mg, Ca, and trace elements.

Urea-containing fertilizer may, in specific embodiments, be urea, formaldehyde urea, anhydrous ammonium, urea ammonium nitrate (UAN) solution, urea sulfur, urea based NPK-fertilizers, or urea ammonium sulfate. Also envisaged is the use of urea as fertilizer. In case urea-containing fertilizers or urea are used or provided, it is particularly preferred that urease inhibitors as defined herein above may be added or additionally be present, or be used at the same time or in connection with the urea-containing fertilizers.

Fertilizers may be provided in any suitable form, e.g. as solid coated or uncoated granules, in liquid or semi-liquid form, as sprayable fertilizer, or via fertigation etc.

Coated fertilizers may be provided with a wide range of materials. Coatings may, for example, be applied to granular or prilled nitrogen (N) fertilizer or to multi-nutrient fertilizers. Typically, urea is used as base material for most coated fertilizers. Alternatively, ammonium or NPK fertilizers are used as base material for coated fertilizers. The present invention, however, also envisages the use of other base materials for coated fertilizers, any one of the fertilizer materials defined herein. In certain embodiments, elemental sulfur may be used as fertilizer coating. The coating may be performed by spraying molten S over urea granules, followed by an application of sealant wax to close fissures in the coating. In a further embodiment, the S layer may be covered with a layer of organic polymers, preferably a thin layer of organic polymers.

Further envisaged coated fertilizers may be provided by reacting resin-based polymers on the surface of the fertilizer granule. A further example of providing coated fertilizers includes the use of low permeability polyethylene polymers in combination with high permeability coatings. In specific embodiments the composition and/or thickness of the fertilizer coating may be adjusted to control, for example, the nutrient release rate for specific applications. The duration of nutrient release from specific fertilizers may vary, e.g. from several weeks to many months. The presence of nitrification inhibitors in a mixture with coated fertilizers may accordingly be adapted. It is, in particular, envisaged that the nutrient release involves or is accompanied by the release of an nitrification inhibitor according to the present invention.

Coated fertilizers may be provided as controlled release fertilizers (CRFs). In specific embodiments these controlled release fertilizers are fully coated urea or N-P-K fertilizers, which are homogeneous and which typically show a pre-defined longevity of release. In further embodiments, the CRFs may be provided as blended controlled release fertilizer products which may contain coated, uncoated and/or slow release components. In certain embodiments, these coated fertilizers may additionally comprise micronutrients. In specific embodiments these fertilizers may show a pre-defined longevity, e.g. in case of N-P-K fertilizers.

Additionally envisaged examples of CRFs include patterned release fertilizers. These fertilizers typically show a pre-defined release patterns (e.g. hi/standard/lo) and a pre-defined longevity. In exemplary embodiments fully coated N-P-K, Mg and micronutrients may be delivered in a patterned release manner.

Also envisaged are double coating approaches or coated fertilizers based on a programmed release.

In further embodiments the fertilizer mixture may be provided as, or may comprise or contain a slow release fertilizer. The fertilizer may, for example, be released over any suitable period of time, e.g. over a period of 1 to 5 months, preferably up to 3 months. Typical examples of ingredients of slow release fertilizers are IBDU (isobutylidenediurea), e.g. containing about 31-32% nitrogen, of which 90% is water insoluble; or UF, i.e. an urea-formaldehyde product which contains about 38% nitrogen of which about 70% may be provided as water insoluble nitrogen; or CDU (crotonylidene diurea) containing about 32% nitrogen; or MU (methylene urea) containing about 38 to 40% nitrogen, of which 25-60% is typically cold water insoluble nitrogen; or MDU (methylene diurea) containing about 40% nitrogen, of which less than 25% is cold water insoluble nitrogen; or MO (methylol urea) containing about 30% nitrogen, which may typically be used in solutions; or DMTU (diimethylene triurea) containing about 40% nitrogen, of which less than 25% is cold water insoluble nitrogen; or TMTU (tri methylene tetraurea), which may be provided as component of UF products; or TMPU (tri methylene pentaurea), which may also be provided as component of UF products; or UT (urea triazone solution) which typically contains about 28% nitrogen. The fertilizer mixture may also be long-term nitrogen-bearing fertiliser containing a mixture of acetylene diurea and at least one other organic nitrogen-bearing fertiliser selected from methylene urea, isobutylidene diurea, crotonylidene diurea, substituted triazones, triuret or mixtures thereof.

Any of the above mentioned fertilizers or fertilizer forms may suitably be combined. For instance, slow release fertilizers may be provided as coated fertilizers. They may also be combined with other fertilizers or fertilizer types. The same applies to the presence of a nitrification inhibitor according to the present invention, which may be adapted to the form and chemical nature of the fertilizer and accordingly be provided such that its release accompanies the release of the fertilizer, e.g. is released at the same time or with the same frequency. The present invention further envisages fertilizer or fertilizer forms as defined herein above in combination with nitrification inhibitors as defined herein above and further in combination with urease inhibitors as defined herein above. Such combinations may be provided as coated or uncoated forms and/or as slow or fast release forms. Preferred are combinations with slow release fertilizers including a coating. In further embodiments, also different release schemes are envisaged, e.g. a slower or a faster release.

The term "fertigation" as used herein refers to the application of fertilizers, optionally soil amendments, and optionally other water-soluble products together with water through an irrigation system to a plant or to the locus where a plant is growing or is intended to grow, or to a soil substituent as defined herein below. For example, liquid fertilizers or dissolved fertilizers may be provided via fertigation directly to a plant or a locus where a plant is growing or is intended to grow. Likewise, nitrification inhibitors according to the present invention, or in combination with additional nitrification inhibitors, may be provided via fertigation to plants or to a locus where a plant is growing or is intended to grow. Fertilizers and nitrification inhibitors according to the present invention, or in combination with additional nitrification inhibitors, may be provided together, e.g. dissolved in the same charge or load of material (typically water) to be irrigated. In further embodiments, fertilizers and nitrification inhibitors may be provided at different points in time. For example, the fertilizer may be fertigated first, followed by the nitrification inhibitor, or preferably, the nitrification inhibitor may be fertigated first, followed by the fertilizer. The time intervals for these activities follow the herein above outlined time intervals for the application of fertilizers and nitrification inhibitors. Also envisaged is a repeated fertigation of fertilizers and nitrification inhibitors according to the present invention, either together or intermittently, e.g. every 2 hours, 6 hours, 12 hours, 24 hours, 2 days, 3 days, 4 days, 5 days, 6 days or more.

In particularly preferred embodiments, the fertilizer is an ammonium-containing fertilizer.

The agrochemical mixture according to the present invention may comprise one fertilizer as defined herein above and one nitrification inhibitor of formula I as defined herein above. In further embodiments, the agrochemical mixture according to the present invention may comprise at least one or more than one fertilizer as defined herein above, e.g. 2, 3, 4, 5, 6, 6, 7, 8, 9, 10 or more different fertilizers (including inorganic, organic and urea-containing fertilizers) and at least one nitrification inhibitor of formula I as defined herein above, preferably one nitrification inhibitor of formula I selected from Table 1.

In another group of embodiments the agrochemical mixture according to the present invention may comprise at least one or more than one nitrification inhibitor of formula I as defined herein above, preferably more than one nitrification inhibitor of formula I selected from Table 1, e.g. 2, 3, 4, 5, 6, 6, 7, 8, 9, 10 or more different nitrification inhibitors as defined herein above or as provided in Table 1 and at least one fertilizer as defined herein above.

The term "at least one" is to be understood as 1, 2, 3 or more of the respective compound selected from the group consisting of fertilizers as defined herein above (also designated as compound A), and nitrification inhibitors of formula I as defined herein above (also designated as compound B).

In addition to at least one fertilizer and at least one nitrification inhibitor as defined herein above, an agrochemical mixture may comprise further ingredients, compounds, active compounds or compositions or the like. For example, the agrochemical mixture may additionally comprise or composed with or on the basis of a carrier, e.g. an agrochemical carrier, preferably as defined herein. In further embodiments, the agrochemical mixture may further comprise at least one pesticidal compound. For example, the agrochemical mixture may additionally comprise at least one herbicidal compound and/or at least one fungicidal compound and/or at least one insecticidal compound.

In further embodiments, the agrochemical mixture may, in addition to the above indicated ingredients, in particular in addition to the nitrification inhibitor of the compound of formula I and the fertilizer, further comprise alternative or additional nitrification inhibitors such as linoleic acid, alpha-linolenic acid, methyl p-coumarate, methyl ferulate, MHPP, Karanjin, brachialacton, p-benzoquinone sorgoleone, nitrapyrin, dicyandiamide (DCD), 3,4-dimethyl pyrazole phosphate (DMPP), 4-amino-1,2,4-triazole hydrochloride (ATC), 1-amido-2-thiourea (ASU), 2-amino-4-chloro-6-methylpyrimidine (AM), 5-ethoxy-3-trichloromethyl-1,2,4-thiodiazole (terrazole), ammoniumthiosulfate (ATU), 3-methylpyrazol (3-MP), 3,5-dimethylpyrazole (DMP), 1,2, 4-triazol and thiourea (TU) and/or sulfathiazole (ST), N-(1H-pyrazolyl-methyl)acetamides such as N-((3(5)-methyl-1H-pyrazole-1-yl)methyl)acetamide, and/or N-(1-H-pyrazolyl-methyl)formamides such as N-((3(5)-methyl-1H-pyrazole-1-yl)methyl formamide, N-(4-chloro-3(5)-methyl-pyrazole-1-ylmethyl)-formamide, or N-(3(5),4-dimethyl-pyrazole-1-ylmethyl)-formamide.

Furthermore, the invention relates to a method for reducing nitrification, comprising treating a plant growing on soil and/or the locus where the plant is growing or is intended to grow with at least one nitrification inhibitor as defined herein above, i.e. with an nitrification inhibitor being a compound of formula I, or a derivative thereof, or a composition comprising said nitrification inhibitor.

The term "plant" is to be understood as a plant of economic importance and/or men-grown plant. In certain embodiments, the term may also be understood as plants which have no or no significant economic importance. The plant is preferably selected from agricultural, silvicultural and horticultural (including ornamental) plants. The term also relates to genetically modified plants.

The term "plant" as used herein further includes all parts of a plant such as germinating seeds, emerging seedlings, plant propagules, herbaceous vegetation as well as established woody plants including all belowground portions (such as the roots) and aboveground portions.

Within the context of the method for reducing nitrification it is assumed that the plant is growing on soil. In specific embodiments, the plant may also grow differently, e.g. in synthetic laboratory environments or on soil substituents, or be supplemented with nutrients, water etc. by artificial or technical means. In such scenarios, the invention envisages a treatment of the zone or area where the nutrients, water etc. are provided to the plant. Also envisaged is that the plant grows in green houses or similar indoor facilities.

The term "locus" is to be understood as any type of environment, soil, soil substituent, area or material where the plant is growing or intended to grow. Preferably, the term relates to soil or soil substituent on which a plant is growing.

In one embodiment, the plant to be treated according to the method of the invention is an agricultural plant. "Agricultural plants" are plants of which a part (e.g. seeds) or all is harvested or cultivated on a commercial scale or which serve as an important source of feed, food, fibers (e.g. cotton, linen), combustibles (e.g. wood, bioethanol, biodiesel, biomass) or other chemical compounds. Preferred agricultural plants are for example cereals, e.g. wheat, rye, barley, triticale, oats, corn, sorghum or rice, beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, oil-seed rape, canola, linseed, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, canola, sugar cane or oil palm; tobacco; nuts; coffee; tea; bananas; vines (table grapes and grape juice grape vines); hop; turf; natural rubber plants.

In a further embodiment, the plant to be treated according to the method of the invention is a horticultural plant. The term "horticultural plants" are to be understood as plants which are commonly used in horticulture, e.g. the cultivation of ornamentals, vegetables and/or fruits. Examples for ornamentals are turf, geranium, pelargonia, petunia, begonia and fuchsia. Examples for vegetables are potatoes, tomatoes, peppers, cucurbits, cucumbers, melons, watermelons, garlic, onions, carrots, cabbage, beans, peas and lettuce and more preferably from tomatoes, onions, peas and lettuce. Examples for fruits are apples, pears, cherries, strawberry, citrus, peaches, apricots and blueberries.

In a further embodiment, the plant to be treated according to the method of the invention is an ornamental plant. "Ornamental plants" are plants which are commonly used in gardening, e.g. in parks, gardens and on balconies. Examples are turf, geranium, pelargonia, petunia, begonia and fuchsia.

In another embodiment of the present invention, the plant to be treated according to the method of the invention is a silvicultural plant. The term "silvicultural plant" is to be understood as trees, more specifically trees used in reforestation or industrial plantations. Industrial plantations generally serve for the commercial production of forest products, such as wood, pulp, paper, rubber tree, Christmas trees, or young trees for gardening purposes. Examples for silvicultural plants are conifers, like pines, in particular Pinus spec., fir and spruce, eucalyptus, tropical trees like teak, rubber tree, oil palm, willow (Salix), in particular Salix spec., poplar (cottonwood), in particular Populus spec., beech, in particular Fagus spec., birch, oil palm, and oak.

The term "plant propagation material" is to be understood to denote all the generative parts of the plant such as seeds and vegetative plant material such as cuttings and tubers (e.g. potatoes), which can be used for the multiplication of the plant. This includes seeds, grains, roots, fruits, tubers, bulbs, rhizomes, cuttings, spores, offshoots, shoots, sprouts and other parts of plants, including seedlings and young plants, which are to be transplanted after germination or after emergence from soil, meristem tissues, single and multiple plant cells and any other plant tissue from which a complete plant can be obtained.

The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073.

The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (*Coeloptera*), two-winged insects (*Diptera*), and moths (*Lepidoptera*) and to nematodes (*Nematoda*). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The term "soil substituent" as used herein refers to a substrate which is able to allow the growth of a plant and does not comprise usual soil ingredients. This substrate is typically an inorganic substrate which may have the function of an inert medium. It may, in certain embodiments, also comprise organic elements or portions. Soil substituents may, for example, be used in hydroculture or hydroponic approaches, i.e. wherein plants are grown in soilless medium and/or aquatic based environments. Examples of suitable soil substituents, which may be used in the context of the present invention, are perlite, gravel, biochar, mineral wool, coconut husk, phyllosilicates, i.e. sheet silicate minerals, typically formed by parallel sheets of silicate tetrahedra with $Si_2O_5$ or a 2:5 ratio, or clay aggregates, in particular expanded clay aggregates with a diameter of about 10 to 40 mm. Particularly preferred is the employment of vermiculite, i.e. a phyllosilicate with 2 tetrahedral sheets for every one octahedral sheet present.

The use of soil substituents may, in specific embodiments, be combined with fertigation or irrigation as defined herein.

In specific embodiments, the treatment may be carried out during all suitable growth stages of a plant as defined herein. For example, the treatment may be carried out during the BBCH principle growth stages.

The term "BBCH principal growth stage" refers to the extended BBCH-scale which is a system for a uniform coding of phenologically similar growth stages of all mono- and dicotyledonous plant species in which the entire developmental cycle of the plants is subdivided into clearly recognizable and distinguishable longer-lasting developmental phases. The BBCH-scale uses a decimal code system, which is divided into principal and secondary growth stages. The abbreviation BBCH derives from the Federal Biological Research Centre for Agriculture and Forestry (Germany), the Bundessortenamt (Germany) and the chemical industry.

In one embodiment the invention relates to a method for reducing nitrification comprising treating a plant growing on soil or soil substituents and/or the locus where the plant is growing or is intended to grow with at least one nitrification inhibitor as defined herein above, i.e. with a nitrification inhibitor being a compound of formula I, or a derivative thereof at a growth stage (GS) between GS 00 and GS>BBCH 99 of the pant (e.g. when fertilizing in fall after harvesting apples) and preferably between GS 00 and GS 65 BBCH of the plant.

In one embodiment the invention relates to a method for reducing nitrification comprising treating a plant growing on soil or soil substituents and/or the locus where the plant is growing or is intended to grow with at least one nitrification inhibitor as defined herein above, i.e. with a nitrification inhibitor being a compound of formula I, or a derivative thereof at a growth stage (GS) between GS 00 to GS 45, preferably between GS 00 and GS 40 BBCH of the plant.

In a preferred embodiment the invention relates to a method for reducing nitrification comprising treating a plant growing on soil or soil substituents and/or the locus where the plant is growing or is intended to grow with at least one nitrification inhibitor as defined herein above, i.e. with a nitrification inhibitor being a compound of formula I, or a derivative thereof at an early growth stage (GS), in particular a GS 00 to GS 05, or GS 00 to GS 10, or GS 00 to GS 15, or GS 00 to GS 20, or GS 00 to GS 25 or GS 00 to GS 33 BBCH of the plant. In particularly preferred embodiments, the method for reducing nitrification comprises treating a plant growing on soil or soil substituents and/or the locus where the plant is growing or is intended to grow with at least one nitrification inhibitor as defined herein above during growth stages including GS 00.

In a further, specific embodiment of the invention, at least one nitrification inhibitor as defined herein above, i.e. a nitrification inhibitor being a compound of formula I, or a derivative thereof is applied to a plant growing on soil or soil substituents and/or the locus where the plant is growing or is intended to grow at a growth stage between GS 00 and GS 55 BBCH, or of the plant.

In a further embodiment of the invention, at least one nitrification inhibitor as defined herein above, i.e. a nitrification inhibitor being a compound of formula I, or a derivative thereof is applied to a plant growing on soil or soil substituents and/or the locus where the plant is growing or is intended to grow at the growth stage between GS 00 and GS 47 BBCH of the plant.

In one embodiment of the invention, at least one nitrification inhibitor as defined herein above, i.e. a nitrification inhibitor being a compound of formula I, or a derivative thereof is applied to a plant growing on soil or soil substituents and/or the locus where the plant is growing or is intended to grow before and at sowing, before emergence, and until harvest (GS 00 to GS 89 BBCH), or at a growth stage (GS) between GS 00 and GS 65 BBCH of the plant.

In a preferred embodiment the invention relates to a method for reducing nitrification comprising treating a plant growing on soil or soil substituents and/or the locus where the plant is growing with at least one nitrification inhibitor as defined herein above, i.e. with a nitrification inhibitor being a compound of formula I, or a derivative thereof wherein the plant and/or the locus where plant is growing or is intended to grow is additionally provided with at least one fertilizer. The fertilizer may be any suitable fertilizer, preferably a fertilizer as defined herein above. Also envisaged is the application of more than one fertilizer, e.g. 2, 3, 4, 5, 6, 7, 8, 9, 10 fertilizers, or of different fertilizer classes or categories.

In specific embodiments of the invention, at least one nitrification inhibitor as defined herein above, i.e. a nitrification inhibitor being a compound of formula I, or a derivative thereof and at least one fertilizer is applied to a plant growing on soil or soil substituents and/or the locus where the plant is growing or is intended to grow at a growth stage between GS 00 and GS 33 BBCH of the plant.

In specific embodiments of the invention, at least one nitrification inhibitor as defined herein above, i.e. a nitrification inhibitor being a compound of formula I, or a derivative thereof and at least one fertilizer is applied to a plant growing on soil or soil substituents and/or the locus where the plant is growing or is intended to grow at a growth stage between GS 00 and GS 55 BBCH of the plant.

In further specific embodiments of the invention, at least one nitrification inhibitor as defined herein above, i.e. a nitrification inhibitor being a compound of formula I, or a derivative thereof and at least one fertilizer is applied to a plant growing on soil or soil substituents and/or the locus where the plant is growing or is intended to grow at sowing, before emergence, or at a growth stage (GS) between GS 00 and GS>BBCH 99 of the pant (e.g. when fertilizing in fall after harvesting apples) and preferably between GS 00 and 65 BBCH of the plant.

According to a preferred embodiment of the present invention the application of said nitrification inhibitor and of said fertilizer as defined herein above is carried out simultaneously or with a time lag. The term "time lag" as used herein means that either the nitrification inhibitor is applied before the fertilizer to the plant growing on soil or soil substituents and/or the locus where the plant is growing or is intended to grow; or the fertilizer is applied before the nitrification inhibitor to the plant growing on soil or soil substituents and/or the locus where the plant is growing or is intended to grow. Such time lag may be any suitable period of time which still allows to provide a nitrification inhibiting effect in the context of fertilizer usage. For example, the time lag may be a time period of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods. Preferably, the time lag is an interval of 1 day, 2 days, 3 days, 1 week, 2 weeks or 3 weeks. The time lag preferably refers to situations in which the nitrification inhibitor as defined above is provided 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months or more or any time period in between the mentioned time periods before the application of a fertilizer as defined herein above.

In another specific embodiment of the invention at least one nitrification inhibitor as defined herein above, i.e. a nitrification inhibitor being a compound of formula I, or a derivative thereof is applied between GS 00 to GS 33 BBCH of the plant, or between GS 00 and GS 65 BBCH of the plant, provided that the application of at least one fertilizer as defined herein above is carried out with a time lag of at least 1 day, e.g. a time lag of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, or more or any time period in between the mentioned time periods. It is preferred that the nitrification inhibitors, which is applied between GS 00 to GS 33 BBCH of the plant, is provided 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks, 11 weeks, or 12 weeks before the application of a fertilizer as defined herein above.

In another specific embodiment of the invention, at least one fertilizer as defined herein above is applied between GS 00 to GS 33 BBCH of the plant or between GS 00 and GS 65 BBCH of the plant, provided that the application of at least one nitrification inhibitor as defined herein above, i.e. of a nitrification inhibitor being a compound of formula I, or a derivative thereof, is carried out with a time lag of at least 1 day, e.g. a time lag of 1 day, 2 days, 3 days, 4 days, 5 days, 6 days, 7 days, 8 days, 9 days, 10 days, 11 days, 12 days, 13 days, 14 days, 3 weeks 4 weeks, 5 weeks, 6 weeks, 7 weeks, 8 weeks, 9 weeks, 10 weeks or more or any time period in between the mentioned time periods.

According to a specific embodiment of the present invention a plant growing on soil or soil substituents and/or the locus where the plant is growing or is intended to grow is treated at least once with a nitrification inhibitor as defined herein above, i.e. with a nitrification inhibitor being a compound of formula I, or a derivative thereof. In a further specific embodiment of the present invention a plant growing on soil or soil substituents and/or the locus where the plant is growing or is intended to grow is treated at least once with a nitrification inhibitor as defined herein above, i.e. with a nitrification inhibitor being a compound of formula I, or a derivative thereof, and at least once with a fertilizer as defined herein above.

The term "at least once" means that the application may be performed one time, or several times, i.e. that a repetition of the treatment with a nitrification inhibitor and/or a fertilizer may be envisaged. Such a repetition may a 2 times, 3 times, 4 times, 5 times, 6 times, 7 times, 8 times, 9 times, 10 times or more frequent repetition of the treatment with a nitrification inhibitor and/or a fertilizer. The repetition of treatment with a nitrification inhibitor and a fertilizer may further be different. For example, while the fertilizer may be applied only once, the nitrification inhibitor may be applied 2 times, 3 times, 4 times etc. Alternatively, while the nitrification inhibitor may be applied only once, the fertilizer may be applied 2 times, 3 times, 4 times etc. Further envisaged are all combination of numerical different numbers of repetitions for the application of a nitrification inhibitor and a fertilizer as defined herein above.

Such a repeated treatment may further be combined with a time lag between the treatment of the nitrification inhibitor and the fertilizer as described above.

The time interval between a first application and second or subsequent application of a nitrification inhibitor and/or a fertilizer may be any suitable interval. This interval may range from a few seconds up to 3 months, e.g. from a few seconds up to 1 month, or from a few seconds up to 2 weeks. In further embodiments, the time interval may range from a few seconds up to 3 days or from 1 second up to 24 hours.

In further specific embodiments, a method for reducing nitrification as described above is carried out by treating a plant growing on soil or soil substituents and/or the locus where the plant is growing or is intended to grow with at least one agrochemical mixture as defined herein above, or with a composition for reducing nitrification as defined herein above.

In another embodiment of the invention, an agrochemical mixture comprising an ammonium- or urea-containing fertilizer and at least one nitrification inhibitor as defined herein above is applied before and at sowing, before emergence, and until GS>BBCH 99 of the pant (e.g. when fertilizing in fall after harvesting apples In case the agrochemical mixture is provided as kit of parts or as non-physical mixture, it may be applied with a time lag between the application of the nitrification inhibitor and the fertilizer or between the application of the nitrification inhibitor a secondary or further ingredient, e.g. a pesticidal compound as mentioned herein above.

In a further embodiment plant propagules are preferably treated simultaneously (together or separately) or subsequently.

The term "propagules" or "plant propagules" is to be understood to denote any structure with the capacity to give rise to a new plant, e.g. a seed, a spore, or a part of the vegetative body capable of independent growth if detached from the parent. In a preferred embodiment, the term "propagules" or "plant propagules" denotes for seed.

For a method as described above, or for a use according to the invention, in particular for seed treatment and in furrow application, the application rates of nitrification inhibitors, i.e. of the compound of formula I are between 0.01 g and 5 kg of active ingredient per hectare, preferably between 1 g and 1 kg of active ingredient per hectare, especially preferred between 50 g and 300 g of active ingredient per hectare depending on different parameters such as the specific active ingredient applied and the plant species treated. In the treatment of seed, amounts of from 0.001 g to 20 g per kg of seed, preferably from 0.01 g to 10 g per kg of seed, more preferably from 0.05 to 2 g per kg of seed of nitrification inhibitors may be generally required.

As a matter of course, if nitrification inhibitors and fertilizers (or other ingredients), or if mixtures thereof are employed, the compounds may be used in an effective and non-phytotoxic amount. This means that they are used in a quantity which allows to obtain the desired effect but which does not give rise to any phytotoxic symptoms on the treated plant or on the plant raised from the treated propagule or treated soil or soil substituents. For the use according to the invention, the application rates of fertilizers may be selected such that the amount of applied N is between 10 kg and 1000 kg per hectare, preferably between 50 kg and 700 kg per hectare.

The nitrification inhibitor compounds according to the invention, e.g. compound I as defined herein above, or derivative thereof as defined herein above can be present in different structural or chemical modifications whose biological activity may differ. They are likewise subject matter of the present invention.

The nitrification inhibitor compounds according to the invention, their N-oxides and/or salts etc. may be converted into customary types of compositions, e.g. agrochemical or agricultural compositions such as solutions, emulsions, suspensions, dusts, powders, pastes and granules.

The composition type depends on the particular intended purpose; in each case, it should ensure a fine and uniform distribution of the compound according to the invention. Examples for composition types are suspensions (SC, 00, FS), emulsifiable concentrates (EC), emulsions (EW, EO, ES), microemulsions (ME), pastes, pastilles, wettable powders or dusts (WP, SP, SS, WS, OP, OS) or granules (GR, FG, GG, MG), which can be watersoluble or wettable, as well as gel formulations for the treatment of plant propagation materials such as seeds (GF). Usually the composition types (e.g. SC, 00, FS, EC, WG, SG, WP, SP, SS, WS, GF) are employed diluted. Composition types such as OP, OS, GR, FG, GG and MG are usually used undiluted.

The compositions are prepared in a known manner (see, for example, U.S. Pat. No. 3,060,084, EP 707 445 (for liquid concentrates), Browning: "Agglomeration", Chemical Engineering, Dec. 4, 1967, 147-48, Perry's Chemical Engineer's Handbook, 4th Ed., McGraw-Hili, New York, 1963, S. 8-57 and ff. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

Compositions or mixtures may also comprise auxiliaries which are customary, for example, in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and inorganic thickeners, bactericides, anti-freezing agents, anti-foaming agents, if appropriate colorants and tackifiers or binders (e.g. for seed treatment formulations). Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalenesulfonic acid (Nekal® types, BASF, GermanY), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof. Examples of suitable thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

In specific embodiments, bactericides may be added for preservation and stabilization of the composition. Examples for suitable bactericides are those based on dichlorophene and benzyl alcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes, e.g. rhodamin B, C. I. pigment red 112, C. I. solvent red 1, pigment blue 15:4, pigment blue 15:3, pigment blue 15:2, pigment blue 15: 1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Furthermore odorous substances may be present in the compositions as defined above. Such odorous substances comprise citronellynitril, citral, zertrahydrolinalool, tetrahydrogeraniol, geranonitril, beta-lonon R, rootanol, linalylacetat, morillol, and p-cresometylether.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding compound of formula I and, if appropriate, further active substances, with at least one solid carrier. Granules, e.g. coated granules, impregnated granules and homogeneous granules, can be prepared by binding the active substances to solid carriers. Examples of such suitable solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g. ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:

i) Water-soluble concentrates (SL, LS) 10 parts by weight of a nitrification inhibitor such as a compound of formula I according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible concentrates (DC) 20 parts by weight of a nitrification inhibitor such as a compound of formula I according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable concentrates (EC) 15 parts by weight of a nitrification inhibitor such as a compound of formula I according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES) 25 parts by weight of a nitrification inhibitor such as a compound of formula I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, 00, FS) In an agitated ball mill, 20 parts by weight of a nitrification inhibitor such as a compound of formula I according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-dispersible granules and water-soluble granules (WG, SG) 50 parts by weight of a nitrification inhibitor such as a compound of formula I according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-dispersible powders and water-soluble powders (WP, SP, SS, WS) 75 parts by weight of a nitrification inhibitor such as a compound of formula I according to the invention are ground in a rotor-stator mill with addition of 25 parts by weight of dispersants, wetting agents and silica gel. Dilution with water gives a stable dispersion or solution of the active substance.

The active substance content of the composition is 75% by weight. viii) Gel (GF) In an agitated ball mill, 20 parts by weight of a nitrification inhibitor such as a compound of formula I according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained. 2. Composition types to be applied undiluted ix) Oustable powders (OP, OS) 5 parts by weight of a nitrification inhibitor such as a compound of formula I according to the invention are ground finely and mixed intimately with 95 parts by weight of finely divided kaolin. This gives a dustable composition having an active substance content of 5% by weight.

x) Granules (GR, FG, GG, MG) 0.5 parts by weight of a nitrification inhibitor such as a compound of formula I according to the invention is ground finely and associated with 99.5 parts by weight of carriers. Current methods are extrusion, spray-drying or the fluidized bed. This gives granules to be applied undiluted having an active substance content of 0.5-10% by weight, preferably an active substance content of 0.5-2% by weight.

xi) ULV solutions (UL) 10 parts by weight of a nitrification inhibitor such as a compound of formula I according to the invention are dissolved in 90 parts by weight of an organic solvent, e.g. xylene. This gives a composition to be applied undiluted having an active substance content of 10% by weight.

The compositions, e.g. agrochemical or agriculatural compositons, generally comprise between 0.01 and 95%, preferably between 0.1 and 90%, most preferably between 0.5 and 90%, by weight of active substance. The active substances are employed in a purity offrom 90% to 100%, preferably from 95% to 100% (according to NMR spectrum).

Water-soluble concentrates (LS), flowable concentrates (FS), powders for dry treatment (OS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds.

These compositions can be applied to plant propagation materials, particularly seeds, diluted or undiluted.

The compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying or treating agrochemical or agricultural compounds or mixtures, or compositions as defined herein, respectively, on to plant propagation material, especially seeds, the plant and/or the locus where the plant is growing or intended to grow are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting. In a preferred embodiment, a suspension-type (FS) composition may be used. Typically, a FS composition may comprise 1-800 g/l of active substance, 1 200 g/l surfactant, o to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring.

The application forms depend entirely on the intended purposes; it is intended to ensure in each case the finest possible distribution of the active substances according to the invention. Aqueous application forms can be prepared from emulsion concentrates, pastes or wettable powders (sprayable powders, oil dispersions) by adding water.

To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 90%, such as from 30 to 80%, e.g. from 35 to 45% or from 65 to 75% by weight of active substance. The active substances may also be used successfully in the ultra-low-volume process (ULV), it being possible to apply compositions comprising over 95% by weight of active substance, or even to apply the active substance without additives.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303C), Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

In a further aspect the invention relates to a method for treating a fertilizer or a composition. This treatment includes the application of a nitrification inhibitor which is a compound of formula I as defined herein above to a fertilizer or a composition. The treatment may accordingly result in the presence of said nitrification inhibitor in a preparation of fertilizers or other compositions. Such treatment may, for example, result in a homogenous distribution of nitrification inhibitors on or in fertilizer preparations. Treatment processes are known to the skilled person and may include, for instance, dressing, coating, pelleting, dusting or soaking. In a specific embodiment, the treatment may be a coating of nitrification inhibitors with fertilizer preparations, or a coating of fertilizers with nitrification inhibitors. The treatment may be based on the use of granulation methods as known to the skilled person, e.g. fluidized bed granulation. The treatment may, in certain embodiments, be performed with a composition comprising the nitrification inhibitor as defined herein above, e.g. comprising besides the inhibitor a carrier or a pesticide or any other suitable additional compound as mentioned above.

In a further specific embodiment, the present invention relates to a method for treating seed or plant propagation material. The term "seed treatment" as used herein refers to or involves steps towards the control of biotic stresses on or in seed and the improvement of shooting and development of plants from seeds. For seed treatment it is evident that a plant suffering from biotic stresses such as fungal or insecticidal attack or which has difficulties obtaining sufficient suitable nitrogen-sources shows reduced germination and emergence leading to poorer plant or crop establishment and vigor, and consequently, to a reduced yield as compared to a plant propagation material which has been subjected to curative or preventive treatment against the relevant pest and which can grow without the damage caused by the biotic stress factor. Methods for treating seed or plant progation material according to the invention thus lead, among other advantages, to an enhanced plant health, a better protection against biotic stresses and an increased plant yield.

Seed treatment methods for applying or treating inventive mixtures and compositions thereof, e.g. compositions or agrochemical compositions as defined herein above, and in particular combinations of nitrification inhibitors as defined herein above and secondary effectors such as pesticides, in particular fungicides, insecticides, nematicides and/or biopesticides and/or biostimulants, to plant propagation material, especially seeds, are known in the art, and include dressing, coating, film coating, pelleting and soaking application methods of the propagation material. Such methods are also applicable to the combinations or compositions according to the invention.

In further embodiments, the treatment of seeds is performed with compositions comprising, besides a nitrification inhibitor according to the present invention, e.g. compositions as defined herein above, a fungicide and an insecticide, or a fungicide and a nematicide, or a fungicide and a biopesticide and/or biostimulant, or an insecticide and a nematicide, or an insecticide and a biopesticide and/or biostimulant, or a nematicide and a biopesticide and/or biostimulant, or a combination of a fungicide, insecticide and nematicide, or a combination of a fungicide, insecticide and biopesticide and/or biostimulant, or a combination of an insecticide, nematicide, and biopesticide etc.

In a preferred embodiment, the agricultural composition or combination comprising a nitrification inhibitor according to the present invention, e.g. as defined herein above, is applied or treated on to the plant propagation material by a method such that the germination is not negatively impacted. Accordingly, examples of suitable methods for applying (or treating) a plant propagation material, such as a seed, is seed dressing, seed coating or seed pelleting and alike. It is preferred that the plant propagation material is a seed, seed piece (i.e. stalk) or seed bulb.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in compositions or mixtures as defined herein and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognizable.

An aspect of the present invention includes application of the composition, e.g. agricultural composition or combination comprising a nitrification inhibitor according to the present invention, e.g. as defined herein above, onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B1 and WO 06/112700.

The composition, e.g. agricultural composition or combination comprising a nitrification inhibitor according to the present invention, e.g. as defined herein above, can also be used in form of a "pill" or "pellet" or a suitable substrate and placing, or sowing, the treated pill, or substrate, next to a plant propagation material. Such techniques are known in the art, particularly in EP1124414, WO 07/67042, and WO 07/67044. Application of the composition, e.g. agricultural composition, or combination comprising a nitrification inhibitor according to the present invention, e.g. as defined herein above, onto plant propagation material also includes protecting the plant propagation material treated with the combination of the present invention by placing one or more pesticide- and nitrification inhibitor (NI)-containing particles next to a pesticide- and NI-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. Such techniques are known in the art, particularly in WO 2005/120226.

Application of the combinations onto the seed also includes controlled release coatings on the seeds, wherein the ingredients of the combinations are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the compound s present in the inventive mixtures in any desired sequence or simultaneously.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil or soil substituents but would include any application practice that would target the seed during the planting process.

Preferably, the treatment occurs before sowing of the seed so that the sown seed has been pre-treated with the combination. In particular, seed coating or seed pelleting are preferred in the treatment of the combinations according to the invention. As a result of the treatment, the ingredients in each combination are adhered on to the seed and therefore available for pest control.

The treated seeds can be stored, handled, sowed and tilled in the same manner as any other active ingredient treated seed.

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. Preferred examples of seed treatment formulation types or soil application for pre-mix compositions are of WS, LS, ES, FS, WG or CS-type.

The compositions in question give, after two-to-tenfold dilution, active components concentrations of from 0.01 to 60% by weight, preferably from 0.1 to 40%, in the ready-to-use preparations. Application can be carried out before or during sowing. Methods for applying or treating compositions or combinations comprising a nitrification inhibitor according to the present invention, e.g. as defined herein above on to plant propagation material, especially seeds include dressing, coating, pelleting, dusting, soaking and in-furrow application methods of the propagation material. Preferably, compositions or combinations comprising a nitrification inhibitor according to the present invention, e.g. as defined herein above are applied on to the plant propagation material by a method such that germination is not induced, e. g. by seed dressing, pelleting, coating and dusting.

Typically, a pre-mix formulation for seed treatment application comprises 0.5 to 99.9 percent, especially 1 to 95 percent, of the desired ingredients, and 99.5 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation. Whereas commercial products will preferably be formulated as concentrates (e.g., pre-mix composition (formulation), the end user will normally employ dilute formulations (e.g. tank mix composition).

When employed in plant protection, the total amounts of active components applied are, depending on the kind of effect desired, from 0.001 to 10 kg per ha, preferably from 0.005 to 2 kg per ha, more preferably from 0.05 to 0.9 kg per ha, in particular from 0.1 to 0.75 kg per ha. The application rates may range from about $1\times10^6$ to $5\times10^{15}$ (or more) CFU/ha. Preferably, the spore concentration is about $1\times10^7$ to about $1\times10^{11}$ CFU/ha. In the case of (entomopathogenic) nematodes as microbial pesticides (e.g. *Steinernema feltiae*), the application rates preferably range inform about $1\times10^5$ to $1\times10^{12}$ (or more), more preferably from $1\times10^8$ to $1\times10^{11}$, even more preferably from $5\times10^8$ to $1\times10^{10}$ individuals (e.g. in the form of eggs, juvenile or any other live stages, preferably in an infetive juvenile stage) per ha.

When employed in plant protection by seed treatment, the amount of compositions or combinations comprising a nitrification inhibitor according to the present invention, e.g. as defined herein above (based on total weight of active components) is in the range from 0.01-10 kg, preferably from 0.1-1000 g, more preferably from 1-100 g per 100 kilogram of plant propagation material (preferably seeds). The application rates with respect to plant propagation material preferably may range from about $1\times10^6$ to $1\times10^{12}$ (or more) CFU/seed. Preferably, the concentration is about $1\times10^6$ to about $1\times10^{11}$ CFU/seed. Alternatively, the application rates with respect to plant propagation material may range from about $1\times10^7$ to $1\times10^{14}$ (or more) CFU per 100 kg of seed, preferably from $1\times10^9$ to about $1\times10^{11}$ CFU per 100 kg of seed.

The present invention is further illustrated by the following examples.

EXAMPLES

Example 1

The compounds of the invention have been tested as follows in terms of the inhibition of nitrification:

100 g soil is filled into 500 ml plastic bottles (e.g. soil sampled from the field) and is moistened to 50% water holding capacity. The soil is incubated at 20° C. for two weeks to activate the microbial biomass. 1 ml test solution, containing the compound in the appropriate concentration (usually 0.3 or 1% of nitrogen N), or DMSO and 10 mg nitrogen in the form of ammoniumsulfate-N is added to the soil and everything mixed well. Bottles are capped but loosely to allow air exchange. The bottles are then incubated at 20° C. for 0 and 14 days.

For analysis, 300 ml of a 1% K2SO4-solution is added to the bottle containing the soil and shaken for 2 hours in a horizontal shaker at 150 rpm. Then the whole solution is filtered through a filter (Macherey-Nagel Filter MN 807 ¼). Ammonium and nitrate content is then analyzed in the filtrate in an autoanalyzer at 550 nm (Merck, AA11). The inhibition (NI@a specified concentration) is calculated as follows:

$$\text{inhibition in \%} = \frac{(NO3 - N_{withoutN\,latendof\,incubation} - NO3 - N_{withN\,latendof\,incubation})}{(NO3 - N_{withoutN\,latendof\,incubation} - NO3 - N_{atbeginning})} \times 100$$

The following compound of general formula I.1(i) has been tested. As described above, the compounds of general formula I.1(i) are present in the form of the two possible annular tautomers.

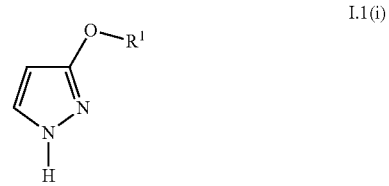

I.1(i)

| No. | R¹ | NI* @ 3% | NI* @ 1% | NI* @ 0.3% |
|-----|----|----|----|----|
| 1 | CH₂CH₃ | 81.6 | 71.5 | 43 |

*In each case the best obtained NI value is provided (only compounds with values >20).

The following compounds of general formula I.3(ii) have been tested. As described above, the compounds of general formula I.1(i) are present in the form of the two possible annular tautomers.

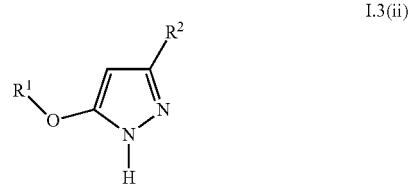

I.3(ii)

| No. | R¹ | R² | NI* @ 1% | NI* @ 0.3% |
|-----|----|----|----|----|
| 2 | CH₃ | CH₃ | 92.1 | 77.3 |
| 3 | CH₂CH₃ | CH₃ | 67.7 | 58.7 |
| 4 | CH₂CH₂CH₃ | CH₃ | 62.3 | 42.7 |
| 5 | allyl | CH₃ | 67.3 | 53.1 |
| 6 | CH₃ | CH₂CH₃ | 48.3 | 26.3 |

*In each case the best obtained NI value is provided (only compounds with values >20).

Further, the following compounds of general formula I.3(i) have been tested.

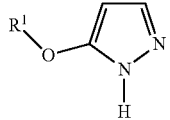

I.3(i)

| No. | R¹ | NI* @ 1% | NI* @ 0.3% |
|---|---|---|---|
| 7 | propargyl | 74.7 | 56.1 |

*In each case the best obtained NI value is provided (only compounds with values >20).

Further, the following compounds of general formula I.3(iii) have been tested.

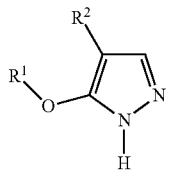

I.3(iii)

| No. | R¹ | R² | NI* @ 1% | NI* @ 0.3% |
|---|---|---|---|---|
| 8 | CH₃ | OCH₃ | 24.4 | — |

*In each case the best obtained NI value is provided (only compounds with values >20).

Furthermore, the following compound corresponding to the formula as displayed below has been tested.

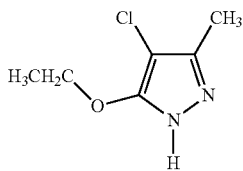

| No. | R¹ | R² | NI* @ 1% | NI* @ 0.3% |
|---|---|---|---|---|
| 9 | CH₂CH₃ | CH₃, Cl | 22.0 | — |

*In each case the best obtained NI value is provided (only compounds with values >20).

The invention claimed is:

1. A method for reducing nitrification, comprising treating a plant growing on soil or soil substituents and/or the locus or soil of soil substituents where the plant is growing with at least one compound of formula 1.3(ii)

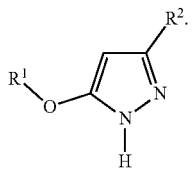

I.3(ii)

or a salt, stereoisomer, tautomer, or N-oxide thereof, wherein
R¹ is CH₃;
R² is CH₃.

2. The method of claim 1, wherein the plant and/or the locus or soil or soil substituents where the plant is growing is additionally provided with a fertilizer.

3. The method of claim 2, wherein the application of said compound of formula I and of said fertilizer is carried out simultaneously or with a time lag.

4. The method of claim 3 wherein the time lag is 1 day, 2 days, 3 days, 1 week, 2 weeks, or 3 weeks.

5. The method of claim 1, wherein the alkoxypyrazole compound of formula 1.3(ii) is present in the form of a pyrazolium salt.

6. The method of claim 5 wherein the pyrazolium salt is a phosphate salt.

7. The method of claim 2, wherein said fertilizer is a solid or liquid ammonium-containing inorganic fertilizer, a solid or liquid organic fertilizer, or a urea-containing fertilizer.

8. The method of claim 7 wherein the fertilizer is selected from the group consisting of an NPK fertilizer, ammonium nitrate, calcium ammonium nitrate, ammonium sulfate nitrate, ammonium sulfate or ammonium phosphate, liquid manure, semi-liquid manure, biogas manure, stable manure and straw manure, worm castings, compost, seaweed or guano, urea, formaldehyde urea, anhydrous ammonium, urea ammonium nitrate (UAN) solution, urea sulphur, urea based NPK-fertilizers, and urea ammonium sulfate.

9. The method of claim 1 wherein said plant is an agricultural plant sorghum; a silvicultural plant; an ornamental plant; or a horticultural plant, each in its natural or in a genetically modified form.

10. The method of claim 9 wherein the agricultural plant or the vegetable is selected from the group consisting of wheat, barley, oat, rye, soybean, corn, potatoes, oilseed rape, canola, sunflower, cotton, sugar cane, sugar beet, rice, spinach, lettuce, asparagus, and cabbages.

11. A method for treating a fertilizer, comprising applying a nitrification inhibitor of formula 1.3(ii)

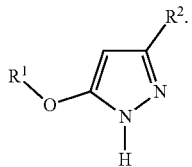

I.3(ii)

or a salt, stereoisomer, tautomer, or N-oxide thereof, wherein
R¹ is CH₃;
R² is CH₃.

12. An agrochemical mixture comprising (i) at least one fertilizer; and (ii) at least one compound of formula 1.3(ii)

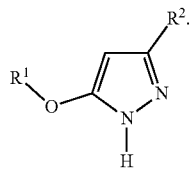
I.3(ii)
or a salt, stereoisomer, tautomer, or N-oxide thereof, wherein
$R^1$ is $CH_3$;
$R^2$ is $CH_3$.
* * * * *